(12) United States Patent
Shibusawa et al.

(10) Patent No.: US 6,937,939 B1
(45) Date of Patent: Aug. 30, 2005

(54) SOIL MEASURING INSTRUMENT, SOIL MEASUREMENT ASSISTING DEVICE AND METHOD, RECORDED MEDIUM ON WHICH A PROGRAM IS RECORDED, RECORDED MEDIUM ON WHICH DATA IS RECORDED, APPLICATION AMOUNT CONTROLLER, APPLICATION AMOUNT DETERMINING DEVICE, METHOD FOR THEM, AND FARM WORKING DETERMINATION ASSISTING SYSTEM

(75) Inventors: Sakae Shibusawa, Fuchu (JP); Shinichi Hirako, Kyoto (JP); Atsushi Hisano, Kyoto (JP); Kizo Yamazaki, Kyoto (JP); Toru Takenobu, Kyoto (JP)

(73) Assignee: Tokyo University of Agriculture and Technology TLO Co., Ltd., (JP)

( * ) Notice: Subject to any disclaimer, the term of this patent is extended or adjusted under 35 U.S.C. 154(b) by 0 days.

(21) Appl. No.: 10/030,402
(22) PCT Filed: Jul. 6, 2000
(86) PCT No.: PCT/JP00/04503

§ 371 (c)(1),
(2), (4) Date: May 20, 2002

(87) PCT Pub. No.: WO01/04627

PCT Pub. Date: Jan. 18, 2001

(30) Foreign Application Priority Data

Jul. 8, 1999 (JP) ................................. 11-195139
Mar. 14, 2000 (JP) ............................... 2000-070158

(51) Int. Cl.⁷ ........................... G06F 19/00; G01V 5/00
(52) U.S. Cl. .......................... 702/22; 702/2; 250/255; 356/336; 356/337; 356/303; 356/326

(58) Field of Search ..................... 702/22, 5, 2; 73/863; 700/282, 283; 356/335, 336, 337, 303, 326; 250/253, 255

(56) References Cited

U.S. PATENT DOCUMENTS 5,044,756 A * 9/1991 Gaultney et al. ........... 356/446

(Continued)

FOREIGN PATENT DOCUMENTS

DE 197 44 973 A1 4/1999 .......... A01C 17/00

(Continued)

OTHER PUBLICATIONS

Bach et al., "Modelling and Model Verification of the Spectral reflectance of Soils Under Varying Moisture Conditions", IEEE, 1994.*

(Continued)

Primary Examiner—Patrick J. Assouad
(74) Attorney, Agent, or Firm—Osha•Liang L.L.P.

(57) ABSTRACT

A model for determining the type of soil, the water content of a soil, and the soil properties, and a soil measurement data storage portion (60) to store therein measurement data necessary to carry out the model and correlated with specific measurement conditions are provided. The water content is measured by a water content measuring portion (57) on the basis of the measurement data fed from a soil sensor (S). The type of soil is determined by a feature extracting portion (56) and a type-of-soil determining portion (58), and the determined type of soil is sent to a determining portion (59). The determining portion (59) determines corresponding conditions and a model according to the type of soil and water content of the measured place received and sets them in a predetermined processing portion. The soil sensor feeds measurement data meeting the measurement conditions to a measurement information processing portion (55), and the processing portion (55) determines the soil properties according to the determined model.

33 Claims, 31 Drawing Sheets

U.S. PATENT DOCUMENTS

| | | | | |
|---|---|---|---|---|
| 5,316,950 A | * | 5/1994 | Apitz et al. | 436/28 |
| 5,323,317 A | | 6/1994 | Hampton et al. | 364/420 |
| 5,355,815 A | * | 10/1994 | Monson | 111/200 |
| 5,461,229 A | * | 10/1995 | Sauter et al. | 250/253 |
| 5,467,271 A | * | 11/1995 | Abel et al. | 702/5 |
| 5,621,669 A | | 4/1997 | Bjornsson | 364/571.01 |
| 5,668,719 A | * | 9/1997 | Bobrov et al. | 702/2 |
| 5,673,637 A | * | 10/1997 | Colburn et al. | 111/118 |
| 5,712,782 A | * | 1/1998 | Weigelt et al. | 701/50 |
| 5,743,343 A | * | 4/1998 | Heller et al. | 175/20 |
| 5,884,224 A | * | 3/1999 | McNabb et al. | 702/2 |
| 5,887,491 A | * | 3/1999 | Monson et al. | 73/864.74 |
| 6,016,713 A | * | 1/2000 | Hale | 73/864.45 |
| 6,035,950 A | * | 3/2000 | Heller et al. | 175/20 |
| 6,041,582 A | * | 3/2000 | Tiede et al. | 56/10.2 A |
| 6,044,324 A | * | 3/2000 | Boerhave et al. | 702/5 |
| 6,070,539 A | * | 6/2000 | Flamme et al. | 111/177 |
| 6,138,590 A | * | 10/2000 | Colburn, Jr. | 111/118 |
| 6,236,907 B1 | * | 5/2001 | Hauwiller et al. | 700/283 |
| 6,324,922 B1 | * | 12/2001 | Hanks | 73/863.12 |
| 6,484,652 B1 | * | 11/2002 | Colburn, Jr. | 111/118 |
| 6,570,999 B1 | * | 5/2003 | Monson | 382/109 |
| 6,597,992 B2 | * | 7/2003 | Rooney et al. | 702/5 |
| 6,606,542 B2 | * | 8/2003 | Hauwiller et al. | 700/283 |
| 6,608,672 B1 | * | 8/2003 | Shibusawa et al. | 356/73 |
| 6,853,937 B2 | * | 2/2005 | Shibusawa et al. | 702/100 |

FOREIGN PATENT DOCUMENTS

| | | | | |
|---|---|---|---|---|
| EP | 0 576 121 A1 | 12/1993 | | A01C 17/00 |
| EP | 0 615 682 A1 | 9/1994 | | A01C 17/00 |
| EP | 0 615 682 B1 | 9/1994 | | A01C 17/00 |
| EP | 0 635 960 A1 | 1/1995 | | H04L 29/06 |
| GB | 2305 045 A | 3/1997 | | G01S 5/14 |
| JP | 51-132887 | 11/1976 | | |
| JP | 11-83627 | 3/1999 | | |
| JP | 11-313594 | 11/1999 | | |
| RU | 1035516 A | 8/1983 | | |
| WO | WO 98/21930 | 5/1998 | | A01B 79/00 |

OTHER PUBLICATIONS

European Search Report dated May 19, 2003, 7 pages.
English Language Abstract for Russian 1035516-A, 2 pages.
European Search Report dated Feb. 11, 2003, 4 pages.
P. Reitz et al., "Investigations on A Particular Yield Mapping System for Combine Harvesters", Computers and Electronics in Agriculture, Amsterdam, NL, vol. 14, No. 2/3, Feb. 1, 1996, pp. 137-150, XP002059527.
H. Auernhammer et al., "GPS for Yield Mapping on Combines", Computers and Electronics in Agriculture, Amsterdam, NL, vol. 11, 1994, pp. 53-68, XP002059528.
Japanese Patent Abstract; Publication No. 11-083627; Published on Mar. 26, 1999.
Japanese Patent Abstract; Publication No. 11-313594; Published on Nov. 16, 1999.

* cited by examiner

FIG.8

Color of Soil and Color-Causing Substances

| Soil Color | Main Coloring Substances | Soil |
|---|---|---|
| Black | * Organic Matter • Humus<br>Iron Sand<br>Black Scoria<br>[ Manganese Speckling, Sulfides ] | Muck Soil •E Peat Soil, Gley Andisol<br>Dark-Colored Andisol ( Humus Volcanic Ash Soil, Andisol)<br>Sandy Soil Containing Large Amount of Iron Sand( Immature )<br>Basalt Volcanic Ejector( Raw Soil ) |
| Red ~ Brown ~ Yellow | * Ferric Oxide Minerals<br>( Iron Oxide )<br>Manganese<br>[ Speckled Iron ] | Red Soil<br>Light-Colored Andisol ( Volcanic Ash Soil, Light-Colored Andisol )<br>Brown Forest Soil, Yellow Soil<br>Dark Red Soil |
| Blue ~ Green | * Ferrous Compounds<br>( Reduced Iron )<br><br>[ Iron Sulfide, Pyrite, Etc.] | Gley Soil( Blue Soil Having Poor Drainage )<br>Strong Gley Soil( Wet Rice Field ), Gley Soil<br>( Semi-Wet Rice Field ) |
| Gray ~ White | * Extremely Small Iron Oxide Content<br>*Oxidization Process of Blue Muddy Layer<br><br>*Accumulation of Salts | Podzol Soil ( Gray Soil ), Degraded Ferro-Deficient Paddy Field<br>Decomposed Granite Soil, Silas, Sandy Soil( White Sand )<br>Gray Lowland Soil( Dry Rice Field )<br>Salty Soil |

( Source : Agricultural Technology System Compiled Soil Fertilizers, Vol.1 Rural Culture Association )

FIG.9

| Input | | | | Output | |
|---|---|---|---|---|---|
| Name of Measurement Object Property | Water Content Ratio | Type of Soil | Measurement Method | Model | Measurement Conditions |
| NO$_3$-N Concentration | Low (3~26%db) Note 1) | Kanto Loam (SILT 28%, CLAY 20%, SAND 52%) | Method 1 : White light is shone onto surface of soil made even by a soil flattening blade, and the reflected light spectrum is measured | NO$_3$-N Concentration= $A + \Sigma B_i \cdot \exp(C_i \cdot X_i)$ Where A, B$_i$, C$_i$ are coefficients. The value of each coefficient is as follows. $Y_i = dX_i / d\lambda$ A=3.96 B1=6.16 E-3 B2=0.241 B3=4.67 E-4 C1=6.27 C2=1.56 C3=6.48 | The amount of reflected light X$_i$ is measured for each of the following wavelengths. (1) 824nm (2) 1280nm (3) 1768nm |
| NO$_3$-N Concentration | High (72~120% db) | Kanto Loam (SILT 28%, CLAY 20%, SAND 52%) | Same as above | NO$_3$-N Concentration= $A + \Sigma B_i \cdot \exp(C_i \cdot X_i)$ $Y_i = dX_i / d\lambda$ Where A, B$_i$, C$_i$ are coefficients. A=0.31 B1=0.243 B2=3.31 E-5 B3=4.64 C1=1.75 C2=7.59 C3=0.127 | The amount of reflected light X$_i$ is measured for each of the following wavelengths. (1) 1286nm (2) 2014nm (3) 2290nm |

Note 1) db is the abbreviation of dry basis, and is the proportion of the weight of water with respect to the weight of solids in the soil.

FIG.10

| Input | | | | Output | |
|---|---|---|---|---|---|
| Name of Measurement Object Property | Water Content Ratio | Type of Soil | Measurement Method | Model | Measurement Conditions |
| Electric Conductivity | Low (2~26%db) | Upland Field | Method 1 | Electric Conductivity= $A+\Sigma(Bi \cdot Xi)$ $Yi=dXi/d\lambda$ Where A, Bi are coefficients. A=128.07 B1= -7.15 B2= -16.29 B3= -7.40 | The amount of reflected light Xi is measured for each of the following wavelengths. (1)2074nm (2)1948nm (3)1776nm |
| Accurate Water Content Ratio | Low (0~26%db) | Upland Field | Method 1 | Y is the second-order derivative of X which is related to $\lambda$. The value obtained by subtracting the average from y is divided by the standard deviation to give a value which forms the standardized value W. Accurate Water Content Ratio= $5.55 \cdot W+13.2$ | The amount of reflected light X is measured for each of the following wavelengths. (1)1450nm |
| Accurate Water Content Ratio | High (72~120% db) | Upland Field | Method 1 | $Y=dX/d\lambda$ The value obtained by subtracting the average from y is divided by the standard deviation to give a value which forms the standardized value W. Accurate Water Content Ratio= $-0.096 \cdot W+9.16$ | The amount of reflected light X is measured for each of the following wavelengths. (1)1850nm |

FIG.11
(a)
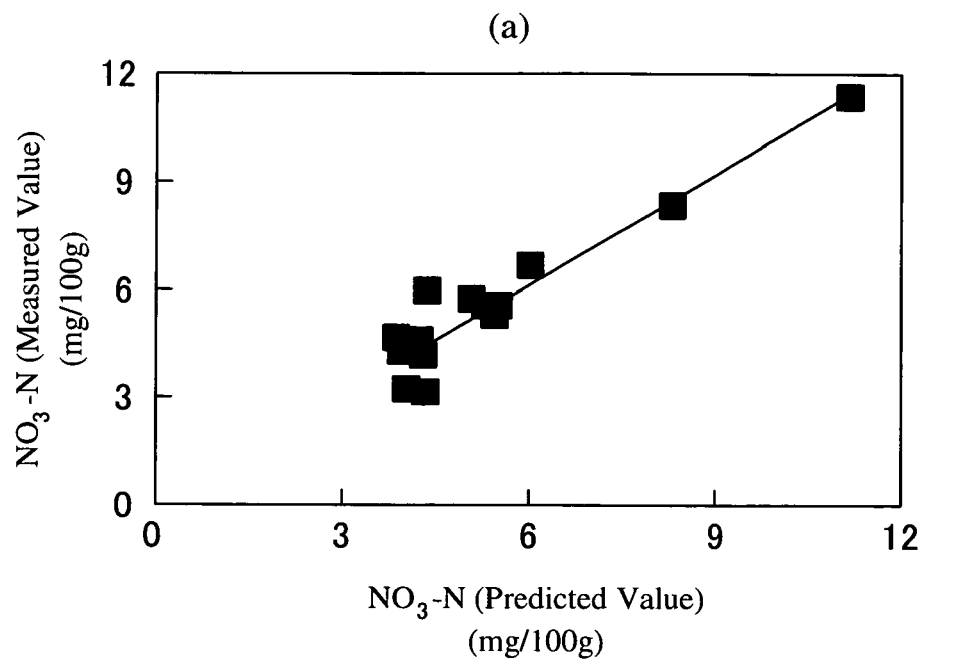
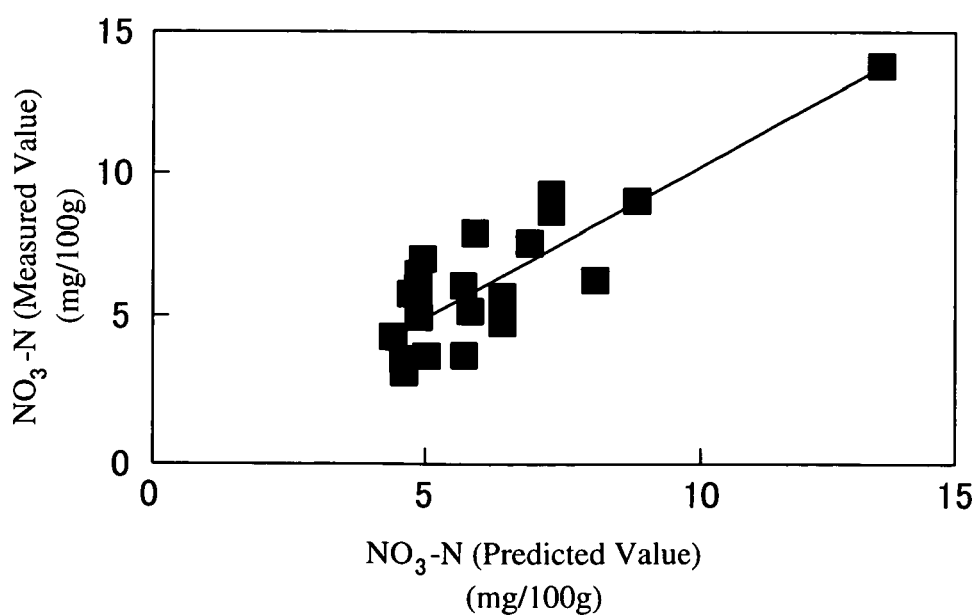

FIG.20

Definitions based on the International Soil Institute Method

| Kind | Definitions : Based on Particle Diameter |
|---|---|
| Clay | Soil Particles Having a Particle Diameter below 0.002 mm |
| Silt | Soil Particles Having a Particle Diameter of 0.002 ~ 0.02 mm |
| Sand | Soil Particles Having a Particle Diameter of 0.02 ~ 2 mm |

FIG.21

| Type of Soil (Main Types) | Definitions | Type of Soil (Subdivided Types) | Definitions |
|---|---|---|---|
| Heavy Clay Type | Clay Content above 45% | Heavy Clay Soil | Clay Content above 45% |
| Clay Type | Clay Content of 25 ~ 45% | Sandy Clay Soil | Sand above 55% |
| | | Light Clay Soil | Sand below 55%+Silt below 45% |
| | | Silty Clay Soil | Silt above 45% |
| Loamy Soil Type | Clay Content of 15 ~ 25% | Sandy Clay Loamy Soil | Sand above 80% |
| | | Clay Loamy Soil | Sand of 55 ~ 85% |
| | | Silty Clay Loamy Soil | Sand below 55% (Silt above 45%) |
| Sandy Soil Type | Clay Content below 15% | Loamy Sandy Soil | Sand above 85%+Clay Content above 5% |
| | | Sandy Soil | Sand below 85%+Clay Content below 5% |
| | | Sandy Loamy Soil | Sand of 65 ~ 85% |
| | | Loamy Soil | Sand below 65%+Silt below 45% |
| | | Silty Loamy Soil | Silt above 45% |

FIG.22

| Contained Substances | | Effect on Color | Specific Example |
|---|---|---|---|
| Iron Compounds | Free Iron | Red, Brown and Yellow become strong | Soil with good exposure to air, such as upland field soil, etc. |
| | Reduced Iron | Blue and Green become strong (Clay of the Gley Layer) | Oxygen Deficient Soil, such as paddy field soil |
| | Small Amount of Iron Compounds | Color becomes Gray, Light Gray | Deposits of volcanic ash and sand (Pyroclastic pumice flow sediment) |
| Manganese Compounds | Free Manganese | Black, Brown and Purple are supplied | For a paddy field with good drainage, the purple layer in the substrate of the surface soil will be visible |
| Humus Content | | Black becomes deep to a large extent | Soil containing a large amount of organic matter, such as Andisol containing a amount of compost, etc. |

Soil Attributes : The color tone becomes stronger when the amount of clay becomes larger.
Water Content : The color tone becomes lighter when the soil becomes drier.
Soil Formation Effects : Brown Woody Soil → Surface layer becomes brown ~ blackish brown( Warm Heavy Rain broad-leaved trees )
Podzol Soil → Bleaching causes color to become white ~ light gray( Cold Needle-leaved trees )
Laterite → Red soil rich in iron and alumina ( tropical rain forest )
Andisol → Black ~ blackish brown ( volcanic ash )
Peat・Muck → Black ~ blackish brown

FIG.27

| Name of Measurement Object Property | Type of Soil | Water Content | Weather Conditions | Soil Measurement Information (Control Data + Soil Measurement Model) | Advertisement Information | Cultivation Recipe + Actual Harvest Results Presentation | Farmland Location Information | Soil Working Instructions Information |
|---|---|---|---|---|---|---|---|---|
| NO₃-N Concentration | Sand Loam | Small | Hot | m1 C1 | Seed Advertisements http:// Agricultural Chemical Advertisements http:// | S1 (Cultivation Recipe + Actual Harvest Results) S2 | P1 (Location, Area, Owner, Farmer, Address) P2, P3 | U1 |
| NO₃-N Concentration | Sand Loam | Large | Cold | m2 C2 | Fertilizer Advertisements http:// | S3 | P4 | U2 |
| Soil Organic Materials | Clay | Small | Dry | m3 C3 | Information on Soil Judgment Services | S4 | P5 | U3 |
| Soil Organic Materials | Clay | Large | Heavy Rain | m4 C4 | Advertisements on crop field Lending and Borrowing | S5 | P6 | U4 |

SOIL MEASURING INSTRUMENT, SOIL MEASUREMENT ASSISTING DEVICE AND METHOD, RECORDED MEDIUM ON WHICH A PROGRAM IS RECORDED, RECORDED MEDIUM ON WHICH DATA IS RECORDED, APPLICATION AMOUNT CONTROLLER, APPLICATION AMOUNT DETERMINING DEVICE, METHOD FOR THEM, AND FARM WORKING DETERMINATION ASSISTING SYSTEM

TECHNICAL FIELD

The present invention is related to a soil measuring apparatus for measuring a soil in real time, a soil measurement assisting device and method, a recording medium on which a program is recorded, a recording medium on which data is recorded, an application amount controller, an application amount determining device, a method for these devices, and a farm working determination assisting system.

PRIOR ART TECHNOLOGY

In order to increase the yield of agricultural products, it is necessary to replenish the deficient components in the soil such as organic components and fertilizers, and plan for the homogenization of the soil of the entire arable land. On the other hand, when such fertilizer or the like is replenished beyond the required amount, there are cases where this is actually not good for the farm products. Further, even in the case where the farm products are not adversely affected by replenishing beyond the required amount, there is an excess portion of fertilizer or the like that is throw away wastefully, and this is not preferred in view of profitability. Furthermore, in the case where environmental preservation is considered, the amount of fertilizer or the like that is consumed should preferably be as little as possible.

In this regard, in recent years, the securing of environmental preservation and profitability has been established as a precondition, and there is wide use of precision field management where the object is to reduce the application amount of agricultural materials, fertilizers, agricultural chemicals and other substances. In order to carry out such management, it is necessary to analyze the components of the soil, and in particular the carrying out of component analysis in real time is desired.

An example of such a soil measurement system for carrying out component analysis in real time is the prior art device disclosed in Japanese Laid-Open Patent Publication No. HEI 11-83627. The invention disclosed in this publication is a device, which analyzes components of a soil from the optical properties of the soil, and the specific structure thereof is shown in FIG. 1.

As shown in the drawing, white light emitted from a light source 1 is shone onto a soil surface 3 having a surface made even by a soil flattening blade 2. The white light (diffusion reflected light) that was diffusion reflected by the soil surface 3 is converged by a converging lens 4 and converged into a light integrating sphere 5. At this time, a reduced image of the soil surface 3 is projected and formed on a light receiving window 6 of the light integrating sphere 5. The light inside the light integrating sphere 5 is guided to a spectrophotometer 7, and such light is dispersed by this spectrophotometer 7. The dispersed light is received by a photo detector 8, and electrical signals corresponding to the intensity of the received light are supplied to a data processor 9. Then, the data processor 9 calculates the light spectrum based on the received electrical signals (received light signals of the photo detector 8), and the soil components are discriminated based on the light spectrum of the reflected dispersed light.

In this way, it becomes possible to accurately measure the optical properties of the soil without being affected by the shape of the soil and unevenness and the like of the soil surface, and the distance from the soil surface is enlarged, and the measurement accuracy is increased.

In order to measure the components, structure, electrical properties, optical properties, chemical properties and the like of the soil in real time, the physical quantities and the like that are detected should have a short measurement time, or should be limited to those quantities that do not require long-time chemical experiments on the soil for the purpose of measurement. In this regard, in the soil measurement system disclosed in the previously mentioned Japanese Laid-Open Patent Publication No. HEI 11-83627, the reflected light spectrum obtained by shining white light onto the soil surface is measured. Namely, because the absorption spectrum of light is fixed depending on the soil components, by measuring the reflected light spectrum with respect to a known illumination spectrum, the concentration of soil components can be measured, and this forms the principle of such system. By utilizing the spectrum of the reflected light in this way, an analysis of the soil components in real time becomes possible, and this point creates a useful invention.

However, from further experiments that have been repeatedly carried out, it is known that even when the component structure of the soil is the same, there will be different spectrums of reflected light depending on the type of soil and the degree of moistness of the soil. In this regard, the distribution of the soil component, which is the measurement object inside the soil, will change depending on the type of soil, for example, as in the case where the soil includes a lot of sand and the case where there is not a lot of sand. Further, depending on the degree of moistness, the soil component, which is measurement object inside the soil, will form other compounds by means of chemical reactions and organism activity, and when analysis is carried out, the existing state of this soil component will change. Due to such causes, there will be changes in the way illumination light shines on the measurement object and changes in the reflection state.

Further, it is difficult for prior art soil measuring apparatus to measure soil properties in real time when the type of soil or the degree of moistness of the soil changes.

It is an object of the present invention to provide a soil measuring apparatus, a soil measurement assisting device and method, a recording medium on which a program is recorded, a recording medium on which data is recorded, an application amount controller, an application amount determining device, a method for these devices, and a farm working determination assisting system which make it possible to easily and quickly establish measurement conditions for measuring soil properties, and establish a model for processing data obtained from a detection means (sensor), and which make it possible to plan for highly accurate and efficient soil measurements even when there are changes in the type of soil or the water content of the soil. Further, it is another object of the present invention to provide a system or assisting system for applying compost and agricultural chemicals and carrying out other soil improvements and the like while preserving the environment, and for easily carrying out processes that are gentle on the environment.

SUMMARY OF THE INVENTION

The soil measuring method according to the present invention uses a soil measuring apparatus to measure properties of a soil, and includes the steps of acquiring measurement data from a soil sensor based on information related to at least the type of soil of a measurement site and the water content contained in the soil, and then inputting said acquired measurement data into a model determined based on information related to said type of soil and the water content in order to calculate soil properties. Further, the "information related to the water content" corresponds to the "water content ratio" in the embodiments.

A soil measuring apparatus suited to executing the method described above is constructed from detecting means which acquires prescribed measurement data from a soil of a measurement object, and measurement information processing means which calculates prescribed soil properties based on said measurement data acquired by said detecting means, wherein a model for processing by said measurement data and said measurement information processing means is determined based on information related to the type of soil of a measurement site and the water content contained in the soil. Further, the detecting means described above corresponds to the "soil sensor S" in the embodiments.

Further, the recording medium according to the present invention which stores a program for executing the processes described above is constructed to make it possible for a computer to read out a stored soil measurement program that includes commands for the computer to execute a process which establishes a model that is determined based on information related to at least the type of soil of a measurement site and the water content contained in the soil, and a process which receives measurement data from a soil sensor, and calculates prescribed soil properties from the received measurement data based on said established model.

For example, by shining light onto the soil of the measurement object, it is possible to calculate soil properties based on the obtained reflected light. Further, the present invention is not limited to utilizing optical properties in this way, and it is possible to calculate soil properties based on physical, chemical or other various kinds of measurement data. In this regard, by acquiring such measurement data by the detecting means or the like, and carrying out information processing based on the model established by the measurement information processing means, it possible to know desired soil properties.

Then, when the types of soil and the water contents are different, even if the soils have the same soil properties, there are situations where the measurement data detected therefrom are different. Conversely, even if the soil properties are different, when the types of soil and water contents are different, there are situations where the obtained measurement data are the same. Namely, the measurement data and the soil properties do not correspond univocally. In this regard, in the present invention, a model suited to the condition of the soil is established based on the type of soil of the measurement object and information related to the water content. Then, soil properties are calculated by inputting measurement data into the established model. In this way, because the measurement information processing means carries out information processing suited to the condition (type of soil, water content, etc.) of the soil of the measurement object, it is possible to calculate soil properties at a high accuracy.

Further, a soil measurement assisting function is preferably provided to determine measurement conditions of measurement data and the like that will be used and said model, and establish such measurement conditions and model in said detecting means and said measurement information processing means. By providing this soil measurement assisting function, the measurement data and the model, which are correlated to the type and water content of the objective soil, are automatically established. Consequently, even when there are changes in the type of soil and water content of the soil, the establishment of measurement conditions (the kind of measurement data to be used, etc.) for measuring soil properties and the establishment of the model can be carried out easily and quickly, and this makes it possible to improve the efficiency of soil measurements.

Further, a creating means is preferably provided to create a soil map based on the soil properties outputted from said measurement information processing means and position information. Further, this creating means corresponds to the "soil map creating portion 50" in the embodiments.

When constructed in this way, because a soil map correlated with the soil properties at each position is created, after such creation, the soil map can be effectively utilized for various analyses and precise field management in the future. Further, as described in the embodiments, the position information can be calculated automatically by using GPS or the like, or specified by manual input. In view of real time processing, it is preferred that the position information also be calculated automatically.

On the other hand, the soil measurement assisting method according to the present invention is an assisting method in an assisting device for a soil measurement apparatus which measures soil properties. Further, this method prepares storage means for storing soil measurement data correlated with at least the type of soil, information related to the water content contained in the soil, a model for calculating soil properties, and measurement conditions for obtaining measurement data that will be inputted into the model. Further, this method acquires at least the type of soil of a measurement site, and information related to the water content contained in the soil, and then accesses said storage means based on the acquired said type of soil and the information related to said water content, reads out the corresponding measurement conditions and model, and outputs said read out measurement conditions and model.

Further, the soil measurement assisting device suited to executing such method is an assisting device for a soil measuring apparatus which measures properties of a soil, and is equipped with storage means for storing soil measurement data correlated with at least the type of soil, information related to the water content contained in the soil, a model for calculating soil properties, and measurement conditions for obtaining measurement data that will be inputted into the model; determining means which acquires at least the type of soil of a measurement site and information related to the water content contained in the soil, accesses said storage means based on the acquired said type of soil and the information related to said water content, and determines the corresponding measurement conditions and model; and means for outputting said read out measurement conditions and model determined by the determining means.

When constructed as described above, by obtaining the type of soil at the measurement site and information related to the water content, it is possible to determine the model and measurement conditions for such type of soil and the like based on the soil measurement data stored in the storage means. Then, by setting the measurement conditions and model in the detecting means and measurement information processing means of the measuring apparatus of claim 2 for example via the outputting means, soil measurements can be carried out efficiently. Further, the type of soil and the information related to the water content may be inputted using either an automatic or manual input method.

Further, even though the model and the measurement data that is inputted into the model were both calculated in the description of each invention described above, both of these do not necessarily need to be calculated, and just one of these may be calculated.

Specifically, the soil measurement assisting method in an assisting device for a soil measuring apparatus which measures properties of a soil is a method that prepares storage means for storing soil measurement data correlated with at least the type of soil, information related to the water content contained in the soil, and measurement conditions for obtaining measurement data that will be inputted into a model for calculating soil properties. Further, this method acquires at least the type of soil of a measurement site, and information related to the water content contained in the soil, and then accesses said storage means based on the acquired said type of soil and the information related to said water content, reads out the corresponding measurement conditions, and outputs said read out measurement conditions.

Further, it is possible to provide a method that prepares storage means for storing soil measurement data correlated with at least the type of soil, information related to the water content contained in the soil, and a model for calculating soil properties; acquires at least the type of soil of a measurement site, and information related to the water content contained in the soil; and then accesses said storage means based on the acquired said type of soil and the information related to said water content, reads out the corresponding model, and outputs said read out model.

Further, in order to execute each of the methods described above, the assisting device for a soil measuring apparatus which measures properties of a soil is equipped with storage means for storing soil measurement data correlated with at least the type of soil, information related to the water content contained in the soil, and measurement conditions for obtaining measurement data that will be inputted into a model for calculating soil properties; determining means which acquires at least the type of soil of a measurement site and information related to the water content contained in the soil, accesses said storage means based on the acquired said type of soil and the information related to said water content, and determines the corresponding measurement conditions; and means for outputting said read out measurement conditions determined by the determining means.

Further, it is possible to construct an assisting device equipped with storage means for storing soil measurement data correlated with at least the type of soil, information related to the water content contained in the soil, and a model for calculating soil properties; determining means which acquires at least the type of soil of a measurement site and information related to the water content contained in the soil, accesses said storage means based on the acquired said type of soil and the information related to said water content, and determines the corresponding model; and means for outputting said read out model determined by the determining means.

Preferably, the assisting device is equipped with a type-of-soil detecting means which calculates said type of soil based on the measurement data obtained by measuring the soil of the measurement object, and supplies such calculated type of soil to said determining means. In this way, because the type of soil is automatically inputted, even people who do not possess knowledge or information on the type of soil can easily carry out soil measurements. Further, even in the case where there are different types of soil mixed together inside the region to be continuously measured due to the transfer of topsoil or the like, by automatically calculating the type of soil, it is possible to carry out analysis of soil properties efficiently at a high accuracy without mistaking the type of soil. Further, the type-of-soil detecting means is formed by "the feature extracting portion 56 and the type-of-soil discriminating portion 58" in the embodiments.

Further, it is also possible to provide a water content information detecting means which calculates information related to the water content based on the measurement data obtained by measuring the soil of the measurement object, and then supplies such calculated information to said determining means. In this way, because the information related to the water content is automatically inputted, it is possible to carry out soil measurements even when the water content is not clearly known. In particular, the water content needs to be known at the point in time of measurements, and preferably such function is provided from the standpoint of carrying out real-time processes rapidly.

Furthermore, as for the specific structure of the means for calculating the water content information, instead of the arrangement described above, for example, it is possible to provide a water content information detecting means that calculates information related to the water content based on measurement data obtained by measuring the soil of the measurement object, and the rough type of soil provided from the clay content of the soil of said measurement object, and then supplies such calculated information to said determining means. Further, the means for calculating the rough type of soil may be one portion of the means for calculating the type of soil as described in the embodiments, namely, a structure may be provided in which the final type of soil is calculated by also utilizing the rough type of soil, or a means for calculating the rough type of soil for calculating the water content information may be separately provided.

Moreover, said type of soil may be calculated from a data base which, holds previous measurements in storage. Further, this data base corresponds to the "GIS data storage portion 63" in the embodiments.

In the case where soil transfer and other soil improvements and the like are not carried out, rapid changes of the type of soil are rare. Accordingly, in the case where there is previously measured data on the type of soil for the soil to be measured, it is possible to utilize such data. In this way, when the previous data of the type of soil is utilized, there is no need to carry out a detection process of the type of soil in real time during measurements, the data processing load is reduced, and the processing time is shortened.

On the other hand, in the case where previous data of the type of soil cannot be utilized, it is possible to use the method described below which is an assisting method in an assisting device for a soil measuring apparatus, which measures properties of a soil. Namely, the assisting method prepares storage means which stores soil measurement data correlated with a model for calculating soil properties, related to optical properties of the soil, and information related to chemical components of the soil. Further, the assisting method acquires at least information related to optical properties of a measurement site; then accesses said storage means based on the acquired said information related to optical properties, and reads out a corresponding model; and then acquires information related to chemical components of the soil at a prescribed site; wherein said model is compensated based on said information related to chemical components.

Further, the recording medium according to the present invention which stores a program for executing each of the processes described above is constructed to make it possible for a computer to read out a stored soil measurement assisting program that includes commands for the computer to execute a process which acquires at least the type of soil of a measurement site, and information related to the water content contained in the soil; a process which, based on the acquired said type of soil and said information related to the water content, accesses a storage region that stores at least the type of soil, the information related to the water content contained in the soil, a model for calculating soil properties, and measurement conditions for acquiring measurement data which will be inputted into the model, and then reads out the corresponding measurement conditions and model; and a process which outputs said read out measurement conditions and model.

Preferably, the recording medium further includes a program which executes at least one process from a process which calculates said type of soil based on measurement data acquired by measuring a soil of a measurement object, and a process which calculates said information related to the water content based on measurement data acquired by measuring a soil of a measurement object.

Further, the soil measuring apparatus according to the present invention is equipped with a soil measuring apparatus main body equipped with detecting means which acquires prescribed measurement data from a soil of a measurement object, and measurement information processing means which calculates prescribed soil properties based on said measurement data acquired by said detecting means; and a soil measurement assisting device which determines, and then outputs to said soil measuring apparatus main body, the type of soil of a measurement site, a model for carrying out processing by said measurement information processing means based on information related to the water content contained in the soil, and measurement conditions for acquiring measurement data which will be inputted into the model; wherein data is communicated between said soil measuring apparatus main body and said soil measurement assisting device by a prescribed communication interface. This invention is achieved by the second embodiment.

In this way, by separately forming the measuring apparatus main body and the assisting device, the assisting device may not be mounted to the means for moving through the field of the measurement object such as a tractor or the like. Further, in the case where a wireless communication means is used, it is possible, for example, for one soil measurement assisting device to cooperate with a plurality of soil measuring apparatuses.

Further, the recording medium according to the present invention can be constructed to store various information that can be read by a computer, including at least the type of soil, information related to the water content contained in the soil, a model for calculating soil properties, and soil measurement data correlated with measurement conditions for acquiring measurement data which will be inputted into the model.

Furthermore, said soil measurement data can be further correlated with the name of the measurement object property, or correlated with the measurement method. Further, the soil measurement data can be correlated with both the name of the measurement object property and the measurement method.

Then, using each of the recording mediums described above, by reading information with a computer, it is possible to easily read out the measurement conditions suited to the condition of the site where the soil is measured and the model, and then use such information for soil measurements, whereby a highly accurate soil analysis can be carried out.

Further, the information stored in the recording medium is not limited to information for carrying out soil measurements such as the model and measurement conditions for calculating soil properties as described above. For example, the recording medium may store at least the type of soil, information related to the water content contained in the soil, soil measurement data for calculating soil properties, and soil correlation information in a constructed state that enables output so as to be readable by a computer.

Further, the soil model data base management system of the present invention is a system which accesses a soil model data base in which at least the type of soil, information related to the water content contained in the soil, soil measurement data for calculating soil properties, and soil correlation information are stored in a constructed state capable of being outputted, and which updates and reads out the stored contents. Further, this system is equipped with a function which supplies recorded information in response to the contents of the request received from a user, and which updates the contents. Further, content updating includes various actions such the correction, supplementation, deletion and the like of the stored information. Further, the supplying of information is not necessarily limited to being carried out for the user who submits a request, and it is also possible to supply information to different users depending on the contents of the request.

In this regard, the soil correlation information includes, for example, seed advertisements, fertilizer advertisements, soil judgment services, cultivation recipes, farmland location information and the like suited to the soil. Namely, when the type of soil and the like are known, because information correlated with this as a key can be accessed, it is possible to efficiently acquire information required for the soil. Further, this is preferred even for the information supplier because it is possible to supply information efficiently to people requiring such information.

Now, because the supply and the like of the information correlated with the soil as described above can be accurately carried out by the soil model data base management system, which controls a related data base, such arrangement is preferred. By carrying out an updating process in order, it is possible to supply the newest information. Further, by increasing the amount of information, it is possible to construct a data base which can be applied to various fields, and which is very convenient to use. At this time, in the case where the supplying of information to the user or the supplying the information for updating from the user is received, when a settlement function for paying a corresponding price in accordance therewith is included, this will form a business for the person executing the soil model data base management system.

Further, the application amount control device of the present invention is a device which, based on soil property values obtained by measurements carried out in real time while moving through a farmland, controls the amount of substances applied to a soil in order to make the soil property values achieve target values, wherein the amount of said substances are determined so that said soil property values of the farmland satisfy environmental standards.

Further, the application amount determining device is equipped with a measuring device which measures soil property values in real time while moving through a farmland, and a control device which carries out a determination so that said property values of the farmland will satisfy environmental standards when determining the amount of substances to be applied to a soil to make the soil property values achieve target values based on said measured soil property values.

Furthermore, in the present invention, it is possible to construct a system from the application amount determining means described above, and an application device which applies said substances based on the results determined by the control device of the application amount determining device.

Further, the application amount control method of the present invention is a processing method in a control device which sends control commands to an application device which applies prescribed substances to a farmland, and this method acquires soil property values obtained by carrying out measurements in real time while moving through the farmland, and then, based on the acquired soil property values, controls the amount of substances applied to the soil within a range that makes said soil property values of the farmland satisfy environmental standards.

Further, another recording medium according to the present invention is constructed to make it possible for a computer to read out an application amount determining program that includes a process which acquires soil property values obtained by measurements carried out in real time while moving through a farmland, and a process which, based on the acquired soil property values, determines the amount of substances to be applied to the soil within a range that makes said soil property values of the farmland satisfy environmental standards held in storage.

In accordance with each of the inventions described above, it is possible to measure soil properties in real time, and because the application amount of required substances can be determined based thereon, suitable soil preparation can be carried out, and an increased harvest amount can be expected. Further, by keeping environmental standards in storage, it is possible to know whether a provisional prescribed application amount of some substance will exceed the environmental standards before application. Accordingly, in such case, it is possible to determine an application amount within a range that satisfies the environmental standards, and then carry out application. Namely, this arrangement forms an invention for achieving an assisting system which makes it possible to simultaneously pursue both "environmental pollution countermeasures" and "soil preparation agriculture" or a system which makes it possible to carry these out.

Further, the farm working determination assisting system according to the present invention is equipped with means for acquiring a soil properties map via communication means from the outside; a data base system which records said soil properties map in a data base in correlation with a work history, and which is capable of searching a work history suited to the inputted soil properties map; and means for creating and outputting a work plan based on the work history suited to said soil properties map.

Explanation of Terms

The "type of soil" is the classification applied to the soil in view of the properties of the soil. Depending on the purpose of classification, there are various classification systems. In the case where the soil is classified for the purpose of soil engineering, the "Japanese Standardized Soil Classification Method" is used. Further, in the case of soil classification for the purpose of farming, the "Agricultural Science Method" is used. In the embodiments of the present invention, the type of soil is defined by the color of the soil, the size of the soil particles, and the texture of the soil for the purpose of agriculture.

Further, in the classification established by the Farmland Soil Classification Committee (1995), there are 24 soil groups and 72 soil subgroups thereof. In actuality, the 72 soil subgroups are used.

The 24 soil groups are man-made soil, peat soil, muck soil, podzol, sand dune regosol, volcanic ejecta immature soil, gley andisol, high humidity andisol, forest andisol, Non-allophane andisol, andisol, lowland paddy soil, gley lowland soil, gray lowland soil, immature lowland soil, brown lowland soil, gley upland soil, debris soil, immature terrestrial soil, dark red soil, red soil, yellow soil, and brown forest soil.

Of course, there is no need to limit classifications to the specific classification method described above, and the type of soil may be determined in accordance with various publicly established or privately determined classifications. Namely, there are various international and individual country soil classification methods depending on the use thereof, the viewpoint of pure soil science and the like. Accordingly, the types of soil established in accordance with an existing classification method may be used. However, these do not always need to correspond to soil classifications based on such soil science classifications, and preferably the classification is assumed to be suited to precision farming methods.

The "information related to the water content contained in the soil" is information for specifying the contained water content, and in the embodiments, this is defined as the water content ratio which is the percentage of water with respect to solids in the soil, but it is also possible to define the water content by a water content percentage which is the percentage of water with respect to the entire soil or in other various ways. Further, instead of a value such as a specific percentage or the like, the water content can be specified qualitatively by such terms as "water content high/low" or "water content high/medium/low" or the like.

The "measurement conditions" are applied when input data for calculating desired soil properties is acquired by the soil sensor, and includes data which controls the established environment of the soil sensor, the sensing operations of the soil sensor, and a process for outputting data obtained by carrying out sensing with the soil sensor. For example, the measurement conditions include many things such as the distance and direction between the soil sensor and the soil surface, the intensity and wavelength of the light or electromagnetic waves shone onto the soil for carrying out soil sensing with the soil sensor, the amplification factor of the amplifier the soil sensor contain, the sampling cycle of the soil sensor, the number of averagings of the information detected by the soil sensor, and the like.

The "model" is information for executing a processing function for calculating (outputting) desired soil properties based on the input of measurement data acquired by the soil sensor and the like. The model includes many things, and representative examples include numerical expressions, subroutines, tables, rules, parameters in prescribed process methods, pointers and the like to the numerical expressions and subroutines, and the like.

Further, the case where the processing function is equipped with the model itself is of course possible, but even when the processing function is not equipped with the model itself, it is possible, for example, to receive inputted measurement data, and then finally implement the processing function. For example, in the case of a pointer as in the example described above, even though it is not itself a processing function, the pointer specifies the storage region or the like where the processing function is stored, and this stored processing function is implemented to calculate soil properties. Namely, in short, in the case where measurement data is inputted for the model, information specified by the model may be used to calculate soil properties.

Further, the information related to the type of soil and the water content of the measurement site are not necessarily limited to information obtained by measuring things of the measurement site at the measurement time. Namely, in the case where these are known in advance, such known data can be utilized. Further, in the case where these are the same within some range, without carrying out measurements for the actual measurement site, it is possible to carry out processing by assuming that data acquired by measuring a different location is the data of the measurement site. In short, any acquisition method can be used so long as it is possible to acquire information related to the type of soil and the water content at the measurement site. Namely, such information can be obtained directly or indirectly, and acquisition can be carried out by various methods of assumed similarity.

The "name of the measurement object property" is information for specifying the soil property to be measured. Further, the "measurement method" is information which specifies what kind of method will be used to acquire measurement data to measure the soil property. The measurement method includes many things, such as the method of measurement, the sensor and measuring apparatus and the like that are used, the method of using these types of devices, the establishment conditions and the like.

BRIEF DESCRIPTION OF THE DRAWINGS

FIG. 8 is a drawing showing the relationship between the color of the soil and the color-causing substances.

FIG. 9 is a drawing (part 1) showing the data structure stored in a soil measurement data storage portion.

FIG. 10 is a drawing (part 2) showing the data structure stored in a soil measurement data storage portion.

FIG. 11 is a graph demonstrating the accuracy of the $NO_3$—N model.

FIG. 20 is a drawing showing the relationship between the kinds of soil and the definitions thereof.

FIG. 21 is a drawing showing the relationship between the types of soil and the definitions thereof.

FIG. 22 is a drawing for describing the effects of various substances contained in the soil on the soil color.

FIG. 27 is a drawing showing an example of a data structure of a soil model data base.

PREFERRED EMBODIMENTS OF THE INVENTION

The preferred embodiments of the present invention will be described with reference to the appended drawings.

Figure 1:
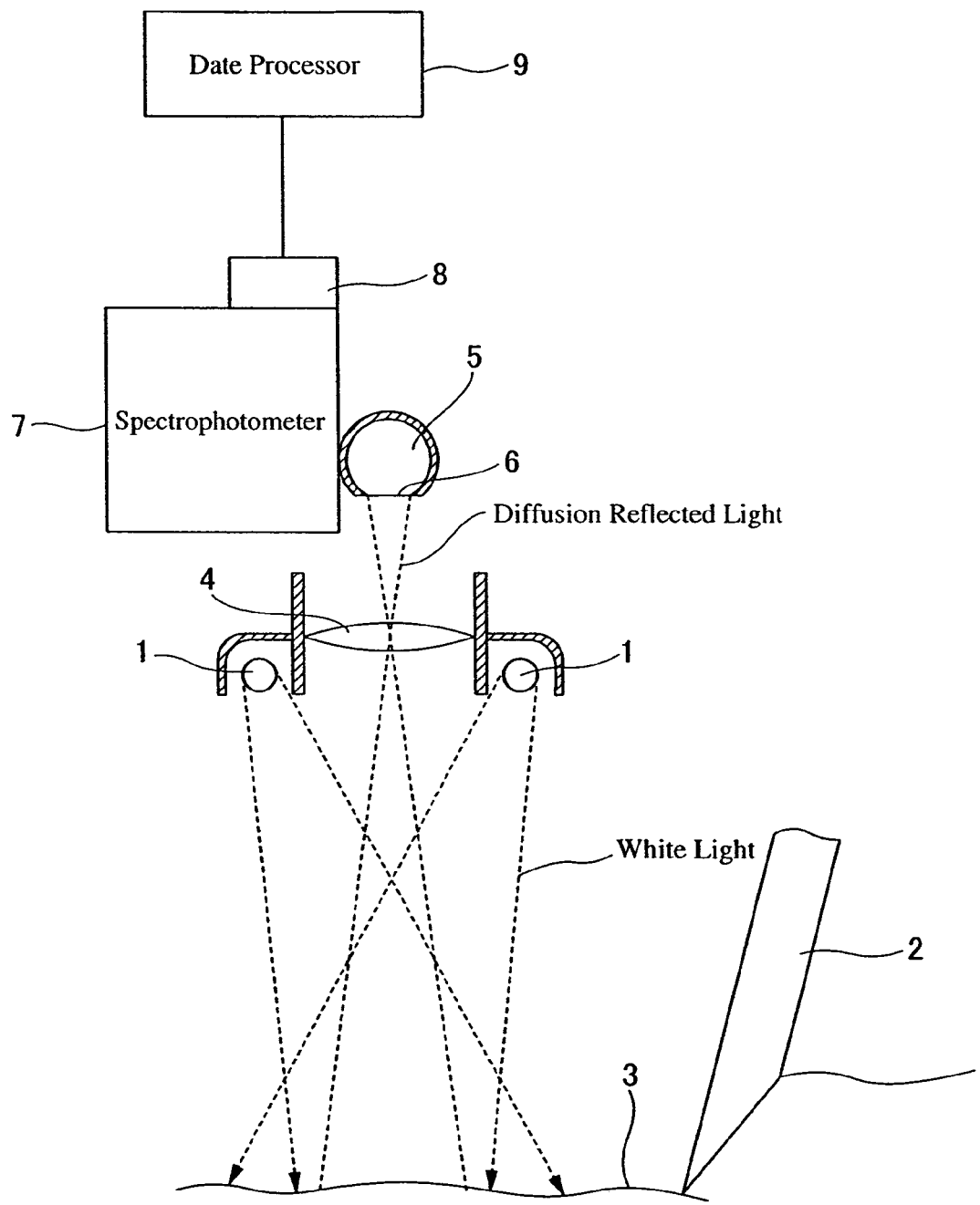
FIG. 1 is a drawing showing a prior art example.
Figure 2:
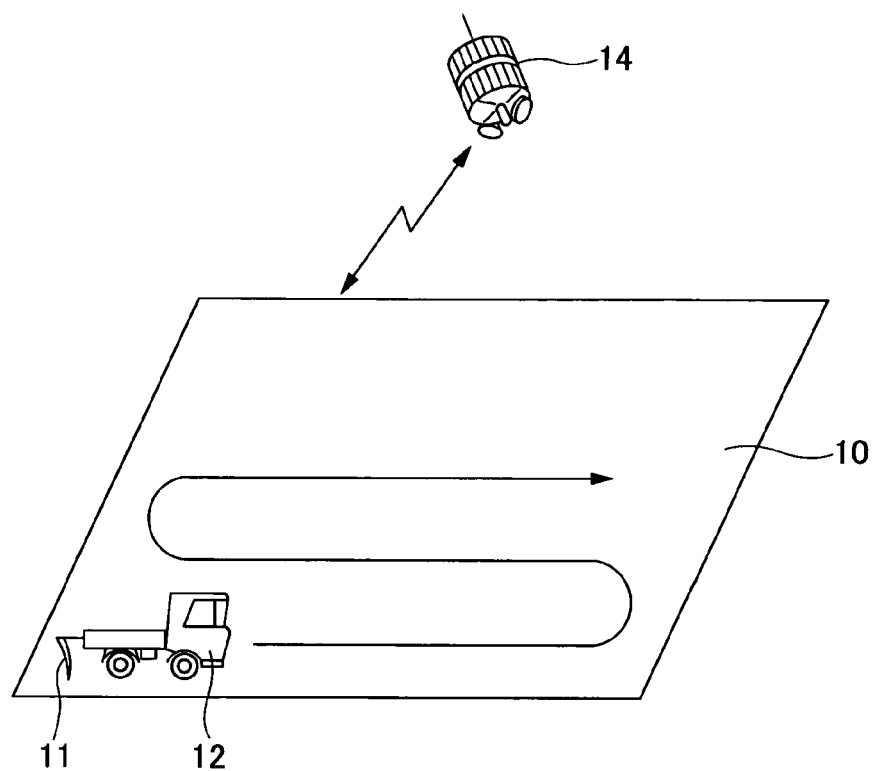
FIG. 2 is a drawing showing an example of the operating state of a soil measuring apparatus to which the present invention is applied.

FIG. 2 is a schematic drawing showing the case where soil properties are measured using a movable-type soil observation vehicle in which the present invention is applied to carry out measurements of the soil properties of each region inside a field 10. As shown in this drawing, a soil measuring apparatus 11 according to the present invention is provided in a tractor 12. In this arrangement, the soil measuring apparatus 11 is used to measure the soil properties at each location inside the field 10 while the tractor 12 moves through the field 10.

Further, the current position of the tractor 12 inside the field 10 is obtained by communication with a GPS (Global Positioning System) satellite 14, and the soil conditions at each region inside the field 10 are measured and recorded based on the measurement results of the soil measuring apparatus 11 which measures soil properties and the current position information obtained from the DGPS satellite 14.

Figure 3:
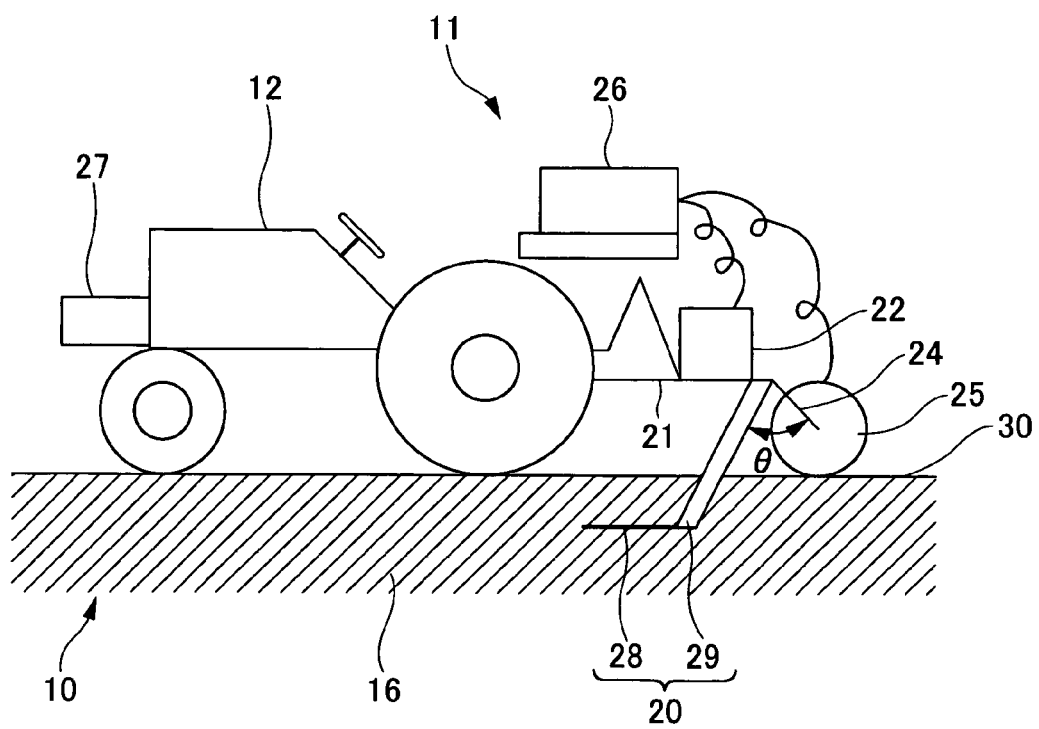
FIG. 3 is a drawing showing the mounted state of a soil measuring apparatus according to the present invention.

FIG. 3 is a schematic view of the soil measuring apparatus 11. In the present embodiment, the soil measuring apparatus 11 mainly detects the optical properties of the soil, and the soil properties are measured based on such optical properties. In this connection, the soil measuring apparatus 11 is mounted on a rear portion of the tractor 12. Further, the soil measuring apparatus 11 includes a main body 20 which excavates a soil 16 of the field 10 while moving through the soil 16, a support frame 21 for connecting the main body 20 to the tractor 12, a spectrophotometer 22 mounted on the support frame 21, a depth measuring wheel 25 which is connected to the upper end of the main body 20 via a support arm 24, and a soil measurement assisting device 26 which carries out data processing based on information supplied from the spectrophotometer 22 and the depth measuring wheel 25 and the like mounted on the tractor 12.

The main body 20 includes a soil excavation portion 28 which excavates the soil 16, and a sensing portion 29 connected to a rear stage of the soil excavation portion 28 to carry out sensing on the soil 16. Further, the spectrophotometer 22 disperses light detected by the sensing portion 29, and a prescribed wavelength portion is extracted to obtain a light spectrum.

Further, the support arm 24 can be rotated forwards and backwards around an upper end portion that is connected to the support frame 21. The depth measuring wheel 25 is mounted to the tip of the support arm 24 in a state that enables free rotation. In this way, because a force acts on the depth measuring wheel 25 in the clockwise direction shown in FIG. 3, namely, in the direction where rotation occurs in the direction that narrows the angle θ formed between the support arm 24 and the upper part of the sensing portion 29, the depth measuring wheel 25 normally makes contact with the top of a soil surface 30. Further, in accordance with the movement of the tractor 12, the depth measuring wheel 25 rotates while being maintained in a contact state with the top of the soil surface 30. Furthermore, when the excavation depth of the main body 20 changes, because the distance between the support frame 21 and the soil surface 30 also changes, the depth measuring wheel 25 undergoes a corresponding movement up or down.

Consequently, the support arm 24 also rotates forwards or backwards in accordance with the up or down movement of the depth measuring wheel 25. Further, as the excavation depth becomes shallower, the depth measuring wheel 25 rises and the angle θ becomes wider. Accordingly, by detecting the angle θ, it is possible to detect the position of the depth measuring wheel 25 and the excavation depth. Furthermore, the angle θ can be measured, for example, by providing a rotation angle detector such as a rotary encoder or the like on the upper rotation axle of the support arm 24. Further, the measurement result of the angle θ is supplied to the soil measurement assisting device 26.

Further, the soil measurement assisting device 26 can be constructed from a personal computer or the like. Furthermore, in the present embodiment, a generator 27 is provided on the front of the tractor 12. This generator 27 is an alternating current generator which generates 100V AC that is used as a driving power source of the soil measurement assisting device 26 and the spectrophotometer 22 and the like.

Figure 4:
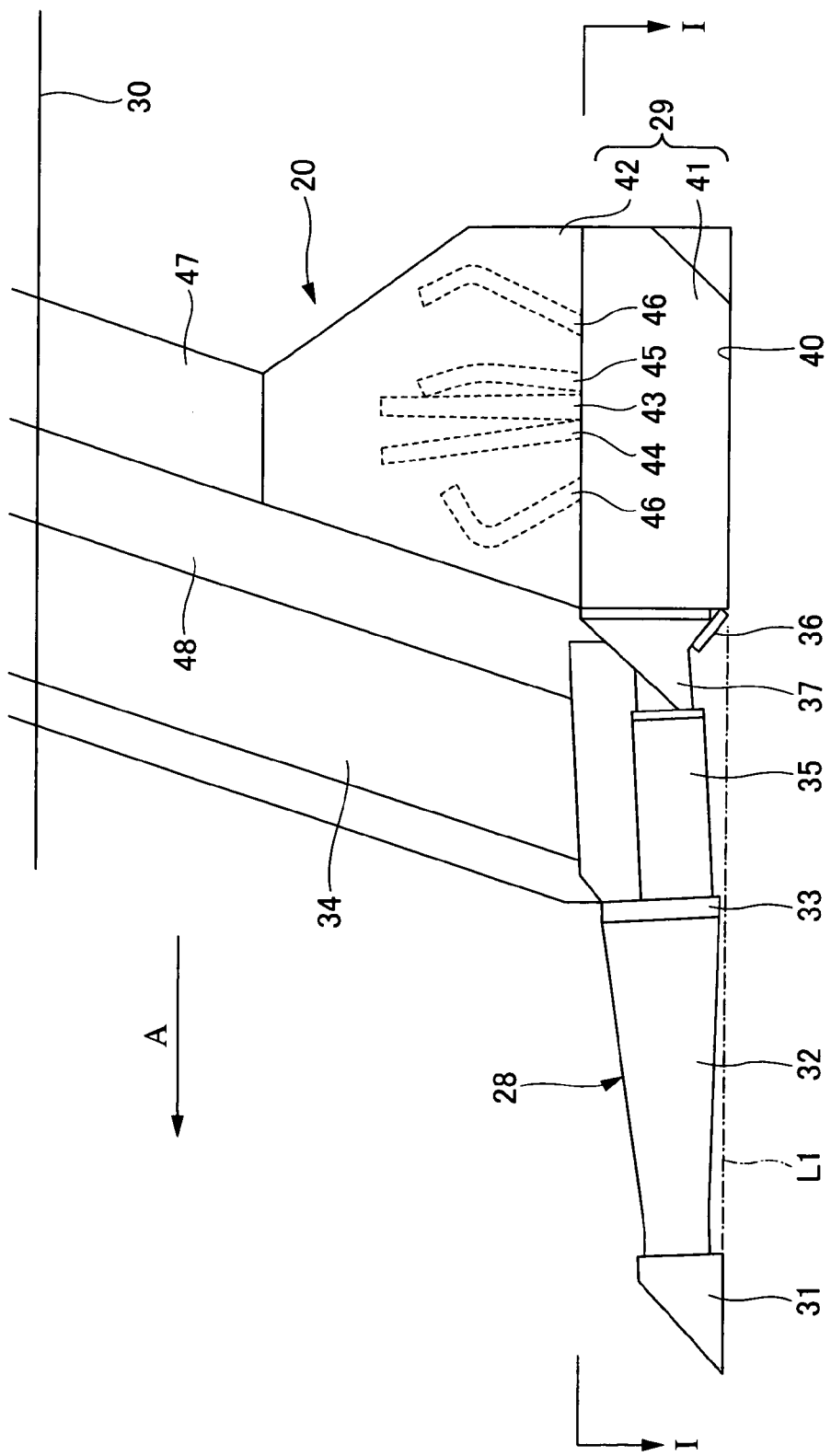
FIG. 4 is an enlarged view showing the soil digging portion and the sensing portion that form the lower portion of the apparatus shown in FIG. 3.
Figure 5:
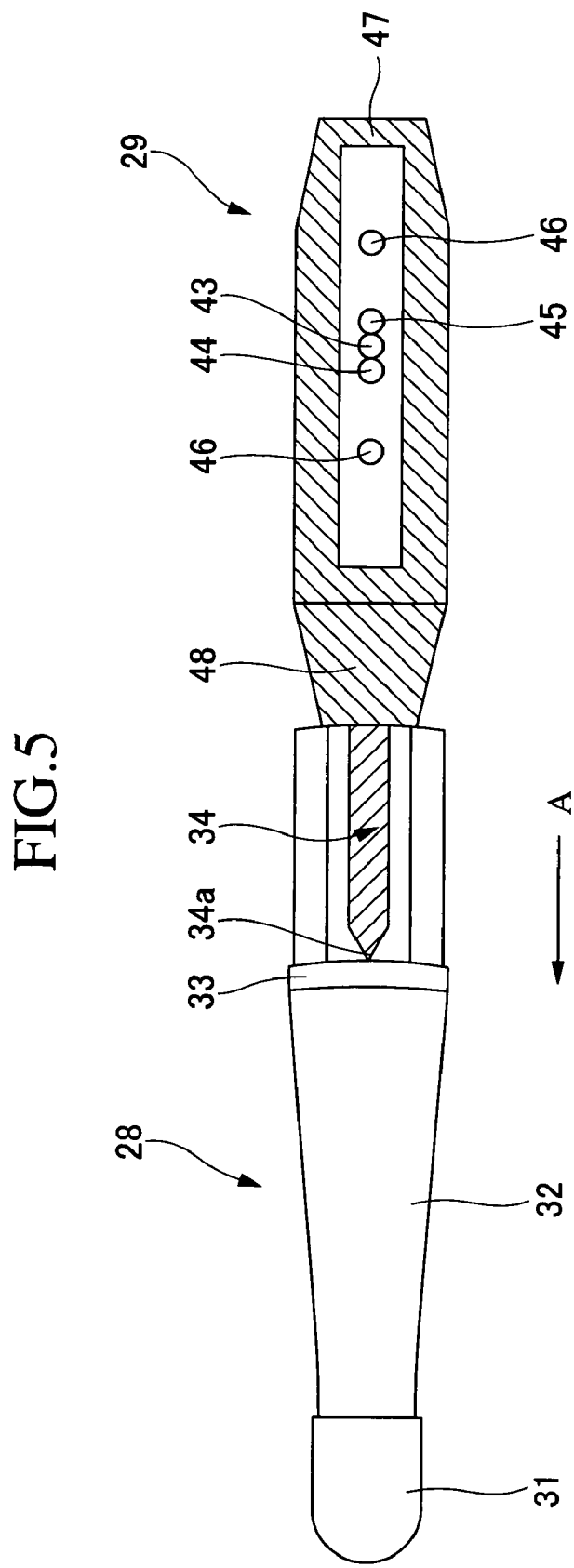
FIG. 5 is a cross-sectional view taken along the arrows I—I of FIG. 4.

FIG. 4 is a side view of the portions of the soil excavation portion 28 and the sensing portion 29, and FIG. 5 is a cross-sectional view of FIG. 4. As shown in this drawing, the soil excavation portion 28 is a portion that excavates the ground in accordance with the movement of the tractor 12, and creates a level soil surface which makes it easy for the sensing portion 29 to carry out sensing on the soil, and the forward movement through the ground is parallel to the soil surface 30.

Specifically, the soil excavation portion 28 is equipped with a first ground penetrating portion 31 having a rough cone shape and a pointed tip, a second ground penetrating portion 32 which is provided so as to be continuous with the first ground penetrating portion 31 and which has a circular cross section that gradually expands, a third ground penetrating portion 35 which is connected to the second ground penetrating portion 32 via a connector 33 and which has a shank 34 mounted to an upper portion, and a fourth ground penetrating portion 37 which is connected to the third ground penetrating portion 35 and the sensing portion 29 and which has a later-described soil flattening blade 36 mounted on the underside.

In this kind of structure, the first ground penetrating portion 31 positioned at the tip of the soil excavation portion 28 has a rough cone shape and the cross section has a rough circular shape, and the cross section of the second ground penetrating portion 32 provided so as to be connected to the first ground penetrating portion 31 also has a rough circular shape. Accordingly, the soil excavation portion 28 excavates a hole having a rough circular shape while moving through the ground. Furthermore, because the cross section has a rough circular shape, the resistance received from the surrounding soil is small, and this makes it possible to move smoothly through the ground without damaging the properties of the surrounding soil that forms the measurement object.

Further, the hole excavated by the first ground penetrating portion 31 has the same rough circular shape described above, and the lower portion (deepest portion side) of this circle is drawn by an arc, and is therefore not flat. On the other hand, as shown in FIG. 4, each of the second ground penetrating portion 32, the third ground penetrating portion 35 and the fourth ground penetrating portion 37 are positioned above a line L1 which connects the bottom surface of the first ground penetrating portion 31 and the bottom surface of the sensing portion 29. Accordingly, the bottom portion (deepest portion side) of the hole, excavated up to the point before the sensing portion 29, has a shape that is unchanged and continues to have a shape that can be drawn by an arc.

However, when a soil having an arc drawn in this way forms the measurement object, it is not possible to carry out soil measurements having a good accuracy. In this regard, a soil flattening blade 36 is mounted to the underside of the fourth ground penetrating portion 37 to level out the bottom portion of the hole that had an arc drawn up to that point.

Further, the shank 34 is positioned at the advancing direction end and is an element that cuts open the soil, and as shown in FIG. 4, the shank 34 is provided so as to be inclined slightly in the opposite direction of the advancing direction A, and the resistance received from the soil as the shank 34 moves forward is small. Furthermore, as shown in FIG. 5, a tip portion 34a thereof is formed to have a wedge shape with an angle of 30 degrees, for example. Consequently, this structure makes it possible to receive minimum resistance while moving forward through the ground, and makes it possible to measure deep portions of the soil.

On the other hand, the sensing portion 29 is constructed from a sensing chamber 41 which is open on the side of a soil surface 40 that forms the measurement object, and a sensor housing portion 42 which houses a plurality of sensor arrays. A CCD camera 43 is provided in the center of the sensor housing portion 42 to take images of the soil surface 40 that forms the measurement object, and color image data is picked up by this CCD camera 43.

Provided on both sides of the CCD camera 43 are a visible light gathering optical fiber 44 for gathering reflected visible light, and a near infrared light gathering optical fiber 45 for gathering reflected near infrared light. Further, an illumination-use optical fiber 46 is provided on both sides of the sensor housing portion 42. Further, light emitted from a light source such as a halogen lamp or the like not shown in the drawings is guided by the illumination-use optical fibers 46 to illuminate the soil surface 40.

In this way, because the light of the detection target has both visible light and near infrared light, the illumination-use optical fibers 46 are designed to pass only light in the wavelength range 400 nm~2400 nm that includes light in the wavelength range 400 nm ~900 nm which is the visible wavelength range, and light in the wavelength range 900 nm ~1700 nm which is the near infrared wavelength range, from the light emitted by the light source.

Further, the near infrared light gathering optical fiber 45 gathers only light in the wavelength range 900 nm ~1700 nm which is the near infrared wavelength band. Further, the visible light gathering optical fiber 44 gathers only light in the wavelength range 400 nm ~900 nm which is the visible wavelength band from the reflected light of the light emitted from the illumination-use optical fibers 46.

Further, a protective case 47 which protects cord-type elements such as optical fibers and the like and which is inclined slightly in the opposite direction of the advancing direction A is provided on the upper portion of the sensing portion 29 to protrude above the ground, and a sensor body support portion 48 is provided between the protective case 47 and the shank 34.

The spectrophotometer 22 is constructed from a visible light spectrometer and a near infrared light spectrometer. Further, the reflected light from the soil surface that is gathered by the visible light gathering optical fiber 44 is sent to the visible light spectrometer. The reflected light from the soil surface that is gathered by the near infrared light gathering optical fiber 45 is sent to the near infrared light spectrometer. In this way, a structure is provided to measure the reception strength in each wavelength range.

Further, each spectrometer is a multichannel-type spectrometer constructed from a photodiode linear array, and this makes it possible to carry out high-speed detection simultaneously on 256 channels in the wavelength range 400 nm~900 nm in the visual region, and 128 channels in the wavelength range 900 nm~1700 nm in the near infrared region.

Figure 6:
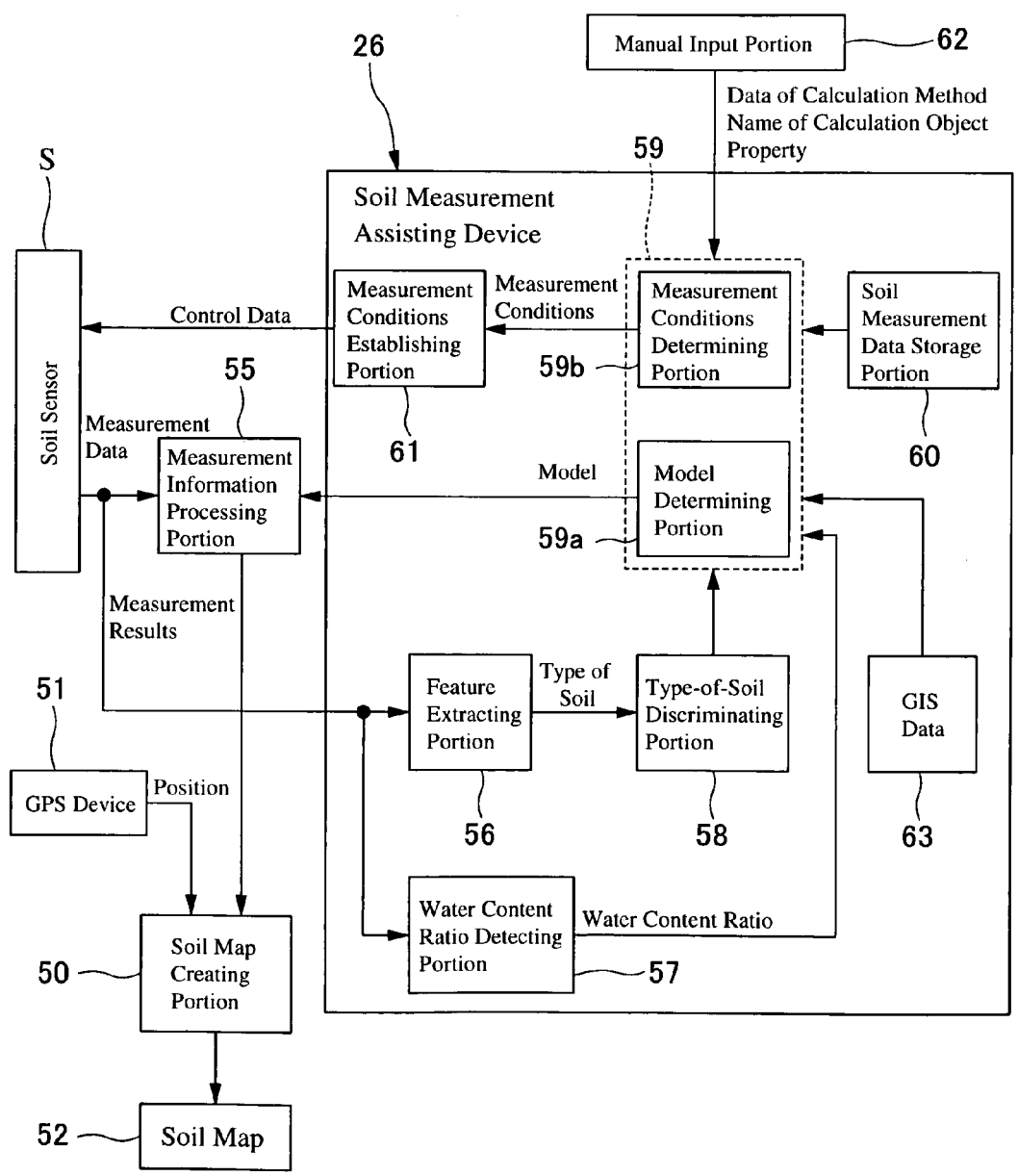
FIG. 6 is a block diagram showing a first embodiment of a soil measuring apparatus and a soil measurement assisting device according to the present invention.

FIG. 6 shows the internal structure of the soil measurement assisting device 26 and the connection state with peripheral devices. First, at the time when soil properties are to be calculated, the soil measurement assisting device 26 determines a model (operation expression) for calculating the soil properties according to the type of soil and the water content ratio of the soil, and the type (measurement conditions) of measurement data required, and then calculates the soil properties from the supplied measurement data based on such model.

Namely, the soil measurement assisting device 26 includes a pre-processing function for determining the above-described model and the like, and a measurement function for calculating the actual soil properties based on the measurement data. In this connection, even inside one field 10, there are situations where the water content ratio is different depending on the location, and there are situations where the type of soil is different in the case where topsoil is brought in or the like, for example. Accordingly, the two functions described above both carry out real time processes at each measurement point.

Of course, in the case where it is known in advance that the type of soil and water content ratio are fixed in the continuous measurement region inside one field 10 or the like, the pre-processing function is carried out once at the beginning, whereafter only the measurement function may be carried out. Furthermore, the pre-processing function and the measurement function do not need to be carried out at every measurement position, and various changes can be carried out such as executing the pre-processing function at any desired timing or the like.

Now, the specific structure is as follows. First, when giving a description regarding the connected state, as shown in the drawing, a soil sensor S measures the optical properties of the soil and supplies the obtained measurement data to the soil measurement assisting device 26. Further, image data taken of the soil surface of the measurement object is also sent. Namely, the soil sensor S corresponds to the spectrophotometer 22 and the sensing portion 29 shown in FIG. 4, FIG. 5 and the like.

The soil measurement assisting device 26 determines the type of soil and the water content ratio based on the received measurement data, and then based on these results, determines the optimum measurement conditions and the model (operation expression) to be used at the time the soil properties are measured. Then, control data is sent to the soil sensor S in order to obtain the determined measurement conditions. Further, the determined measurement model is supplied to a measurement information processing portion 55 which carries out the essential measurement function. Then, the measurement data outputted from the soil sensor S is supplied to the measurement information processing portion 55, and the soil properties are measured based on the measurement model established therein, and then such results are supplied to a soil map creating portion 50.

Further, the soil measuring apparatus is equipped with a GPS device 51 which analyzes received DGPS signals to detect the current position where the apparatus is located, and this position information is supplied to the soil map creating portion 50. Then, the soil map creating portion 50 creates a soil map correlated with the position data and the soil properties, and this map is stored in a soil map storage portion 52. This soil map storage portion 52 may be an internal storage means such as a hard disk or the like of a personal computer, or an external storage means such as a MO, FD, PC card or the like.

Next, the internal structure of the soil measurement assisting device 26 will be described. First, the soil measurement assisting device 26 includes a feature extracting portion 56 for discriminating the type of soil, and a water content ratio detecting portion 57, and the measurement data (mainly wavelength spectrum data) outputted from the soil sensor S is sent to these feature extracting portion 56 and water content ratio detecting portion 57.

Then, the feature quantity extracted by the feature extracting portion 56 is supplied to a next stage type-of-soil discriminating portion 58, and the type of soil at the current position of the soil measuring apparatus is calculated. Further, the calculated type of soil is supplied to a determining portion 59. In the present embodiment, the type of soil is determined based on obtained color image data taken of the soil surface of the measurement object, and the water content ratio is measured (as described later) based on the reflected light intensity of a prescribed wavelength.

From the supplied type of soil and the water content ratio, the determining portion 59 accesses data for soil measurements stored in a soil measurement data storage portion 60, and determines a model suited to carrying out soil measurements, and measurement conditions for obtaining required measurement data. Namely, the model is determined by a model determining portion 59a, and the determined model is supplied to the measurement information processing portion 55. Further, the measurement conditions are determined by a measurement conditions determining portion 59b, and the determined measurement conditions are supplied to a measurement conditions establishing portion 61.

Then, the measurement conditions establishing portion 61 outputs control data which makes the measurement data supplied to the measurement information processing portion 55 from the soil sensor S compatible with the determined measurement conditions. The control data for controlling the soil sensor includes data which indicates the wavelength band requiring output in the light spectrum of the reflected light, data (e.g., the sample number for averaging) for controlling smoothing for noise elimination and the like.

In accordance with the model supplied from the model determining portion 59a, the measurement information processing portion 61 receives desired measurement data established by the above-described control data from the soil sensor S, and carries out data processing to calculate the soil properties of the measurement object. Then, these calculated measurement results, namely the soil properties are outputted to the soil map creating portion 50.

Furthermore, as described above, the measurement data supplied to the measurement information processing portion 55 executes the pre-processing function, and is established based on the determined measurement conditions. On the other hand, the measurement data supplied to the feature extracting portion 56 and the water content ratio detecting portion 57 is suited to the detection of the type of soil and the water content ratio. Therefore, even though the input of both types are "measurement data," there are situations where the specific contents are different (of course, there are also cases where they are the same).

Next, a detailed description of each portion will be described. First, the water content ratio detecting portion 57 determines the water content ratio based on the reflected light having a wavelength of 1,850 nm. Namely, 1,850 nm is one absorption band of water, and by measuring the intensity of light having a wavelength of 1,850 nm in the reflected light from the soil surface at known different water content ratios, the correlation between the water content ratios and the standardized values of the first-order derivatives of such light intensities can be calculated to give properties like those shown in FIG. 7.

In this regard, the first-order derivative can be calculated from the light intensity of the 1,850 nm wavelength and one or a plurality of wavelengths before and after the 1,850 nm wavelength. Further, in the case of conversion where the mean is set at 0 and the standard deviation is set at 1, and where x is the measurement value, m is the average value of the measurement value, and σ is the standard deviation, the standardized value is calculated by the following:

standardized value=$(x-m)/\sigma$

Further, the water content ratio is the percentage of the weight of the water portion with respect to the weight of the solid portion.

Figure 7:
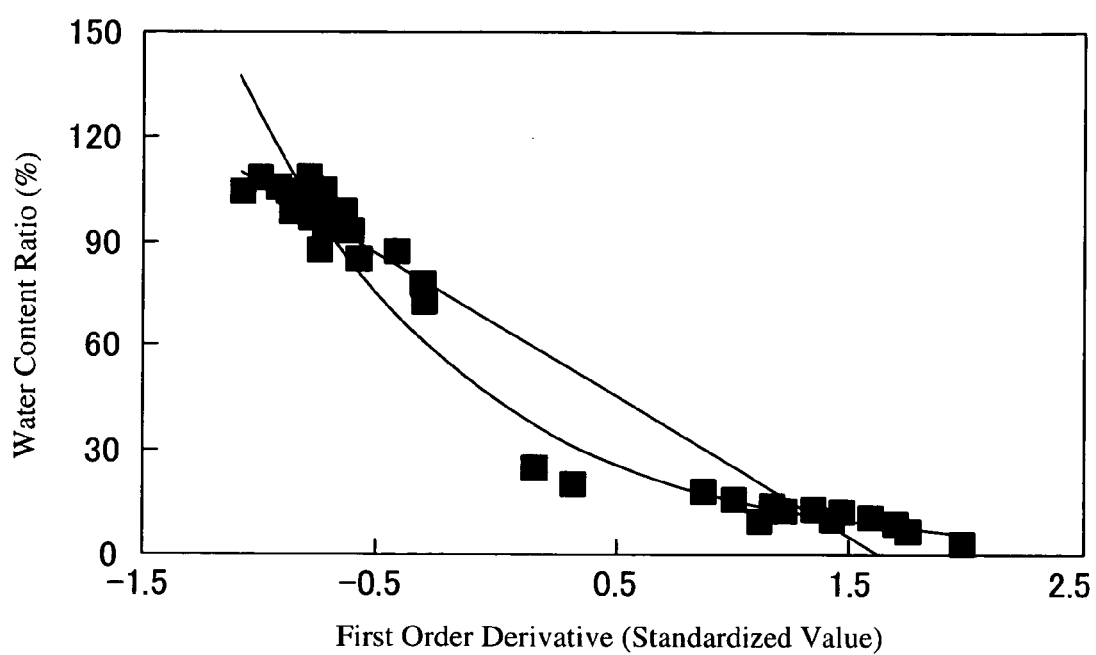
FIG. 7 is a graph for describing the results of a water content ratio determining portion.

As is clear from FIG. 7, the standardized values of the first-order derivatives are negative (in the range −0.5~−1.3) when the water content ratio is high, and the standardized values of the first-order derivatives are positive (in the range 0~2) when the water content ratio is low. Further, in the correlation between the first-order derivative and the water content ratio, coefficient of determination $R^2$ is calculated to be 0.940 by the linear equation given below, and when the exponential function given below is applied, $R^2$ becomes 0.968. In this way, the water content ratio can be predicted to have an accuracy of ±5%.

$y=-39.9x+64.7$ $\rightarrow R^2=0.940$ $y=43.6e^{-1.05x}$ $\rightarrow R^2=0.968$ Accordingly, the water content ratio detecting portion 57 stores the above-described correlation equations (e.g., the exponential function equation), the standard deviation for calculating the standardized values, and the average values, calculates the standardized values of the first-order derivatives from the quantity of reflected light of a prescribed wavelength including 1,850 nm which is the supplied measurement data, and can calculate the water content ratio y by substituting the standardized values into the correlation equations. Then, the calculated water content ratio y is sent to the determining portion 59.

Further, because the above-described correlation forms an intrinsic element of the measuring device, experiments are carried out previously with the used measuring device, the correlation equations and the data for calculating the standardized values are calculated, and this information is set in the water content ratio detecting portion 57. Further, it is of course possible to carry out the first-order derivatives and the standardization at the soil sensor S side, with the results thereof being received by the water content ratio detecting portion 57. Further, there are cases where the water content ratio can be calculated with good accuracy without carrying out a standardization process.

The discrimination of the type of soil in the present embodiment is determined based on the color of the soil surface. Namely, the color of the soil is determined by the structural substances, and in particular, is determined by the quantity and formula of organic substances and iron compounds which form the coloring agents. In this connection, FIG. 8 shows an example of the relationship between the color, the coloring substances and the soil.

In this way, the coloring substances present in the soil are understood from the color, and in the case where a plurality of colors are mixed together, the abundance of each coloring substance can be estimated from the abundance ratios of the mixed colors. By such means, the structural substances contained in the soil are identified from the color state of the soil surface, and the type of soil can be estimated from the abundance ratios.

In this regard, in the feature extracting portion 56, an image process is carried out on the supplied image data, and the color components present in the image data and the abundance ratios thereof are extracted. Then, the extracted color components and abundance ratios are sent to the type-of-soil discriminating portion 58. The type-of-soil discriminating portion 58 prepares a table correlated with the type of soil and the feature quantity (color component, abundance ratio) created based on related information like that shown in FIG. 8 described above, and then refers to the table based on the received feature in order to extract the relevant type of soil. Then, the extracted type of soil is sent to the determining portion 59.

The determining portion 59 receives the name of the soil property of the measurement object and data of the measurement method inputted by an operator via a manual input portion 62, and based on the water content ratio and type of soil automatically calculated as described above, accesses the soil measurement data storage portion 60, and determines the measurement conditions and model.

Further, in the present embodiment, the manual input portion 62 can be used to input the type of soil and the water content ratio to the determining portion 59. Namely, it is possible to cope with both the case where the type of soil and water content ratio are established automatically based on the measurement data as described above, and the case where the type of soil and water content ratio are inputted manually.

Further, recently a plurality of sites for each farm in the entire country have been sampled to determine the type of soil, and this data has been put into a data base. The data stored in this data base is called GIS (Geographic Information System) data. In this regard, this GIS data is kept in storage in a GIS data storage portion 63, and it is possible to extract the type of soil of the measurement object from this stored GIS data, and then supply such information to the determining portion 59. The position information required when reading out the GIS data of this case can be specified manually, or it is possible to use an arrangement in which detection is carried out by the GPS device 51.

Now, a description of the soil measurement data will be given with reference to the data structure shown in FIG. 9 and FIG. 10. As shown in these drawings, the name of the measurement object property, the water content ratio, the type of soil and the measurement method form four parameters at the input side, and a table correlated with two types of information comprised of the measurement conditions and the model specified by the four parameters of the input side are formed at the output side.

Namely, the model determining portion 59a searches the input side based on the two types of data supplied from an operator and the two types of data (inputted manually or inputted from GIS data are also possible) comprised of the type of soil and the water content ratio supplied from the type-of-soil discriminating portion 58 and the water content ratio detecting portion 57, and when relevant information is detected, the column of the model of the output side correlated with such information is read out and sent to the measurement information processing portion 55. In the same manner, the measurement conditions determining portion 59b searches the input side based on the above-described four types of data supplied manually and automatically, and when relevant information is detected, the column of the measurement conditions of the output side correlated with such information is read out and sent to the measurement conditions establishing portion 61. Namely, in the present embodiment, the determining portion 59 refers to the table stored in the soil measurement data storage portion 60 based on supplied information, and includes a function for extracting and outputting relevant information.

Further, in FIG. 9 and FIG. 10, the four types of input are the (1) name of the measurement object property, the (2) water content ratio, the (3) type of soil, and the (4) measurement method. In carrying out the measurement of the soil property, the (1) name of the measurement object property and the (4) measurement method are considered to be normally fixed for one farmland. In this case, the (1) name of the measurement object property and the (4) measurement method are not needed in the index for searching the tables of FIG. 9 and FIG. 10. However, in the case where the soil property of the measurement object and the measurement sensor are changed, all the items (1)~(4) are needed for a search of the tables of FIG. 9 and FIG. 10.

Next, a description of each item of the soil measurement tables will be given. The name of the measurement object property specifies the type of property to be measured from the soil properties. In the examples shown in the drawings, the concentration of $NO_3$—N, the electric conductivity and the water content ratio are shown as the property, but in addition to these, the property can be a chemical component such as phosphorus, potassium, manganese, magnesium, iron, boron, silicon or the like, or a physical quantity such as the organic matter content, the water permeability, the hardness, the pH or the like.

Further, the measurement method specifies the method that is used to acquire the measurement data, and this method is different depending on the sensor and the measurement apparatus and the like that are used. The method 1 shown in the drawings is the measurement method that uses the apparatus of the embodiment described above. Further, the water content ratio and type of soil of the input side are the same as those described in the embodiment given above.

The measurement object property is calculated using the model based on measurement data supplied from the soil sensor S, and in the present embodiment, data specifying the operation expression is stored. This operation expression can use exponential multiple regression, linear multiple regression or the like. Further, by actually carrying out sampling on known soils to obtain correlation data of the value of the measurement object property with respect to the measurement data, such operation expression can be determined based on the obtained correlation. Further, the measurement conditions include the type of measurement data required for acquiring the variables in the operation expression of the model, and in the case of a light spectrum, includes wavelength data for sampling.

Now, a description will be given for the model mentioned above. In the case where the type of soil is Kanto loam and the water content ratio is low, the $NO_3$—N concentration can be calculated by the following:

$$A + \Sigma Bi^* \exp(Ci^* Yi)$$

Here, Yi is the first-order derivative of the wavelength Xi. Normally, a second-order derivative is used, but by using a first-order derivative, it is possible to accurately calculate the $NO_3$—N concentration. Further, Bi and Ci are respective variables, and in the present example i has a value of 1 to 3.

Namely, the value of the calculated $NO_3$—N concentration is the value obtained by adding the coefficient A to the total of the value calculated from B1, C1 and the first-order derivative value of the quantity of reflected light at the 824 nm wavelength shown by the measurement condition (1) when i=1, the value calculated from B2, C2 and the first-order derivative value of the quantity of reflected light at the 1,280 nm wavelength shown by the measurement condition (2) when i=2, and the value calculated from B3, C3 and the first-order derivative value of the quantity of reflected light at the 1,768 nm wavelength shown by the measurement condition (3) when i=3.

The correlation between the value (predicted value) of the $NO_3$—N concentration calculated by the above-described expression and the actual value (measured value) of the $NO_3$—N concentration is like that shown in FIG. 11(a). As is clear from this drawing, the values lie roughly on a straight line, and the coefficient of determination $R^2$ has a high level value of 0.903.

Further, in the model for the case where the type of soil is the same Kanto loam with a high water content ratio, the operation expression is the same as that for the low water content ratio case described above, where i has the same values 1 to 3. However, the specific values of the coefficients A, Bi, Ci and the three wavelengths established as the measurement conditions are different. In this way, by establishing a model (operation expression) in accordance with the water content ratio, it is possible to obtain the correlation between the value (predicted value) of the $NO_3$—N concentration calculated by such expression and the actual value (measured value) of the $NO_3$—N concentration, as shown in FIG. 11(b). As is clear from this drawing, the values lie roughly on a straight line, and the obtained results indicate that the coefficient of determination $R^2$ is 0.732.

With this model, in view of the fact that the calculation of the $NO_3$—N concentration was not possible in the prior art though the coefficient of determination $R^2$ is rather small for high water content ratios, the present embodiment makes it possible to calculate the $NO_3$—N concentration by direct operation, and this achieves superior results.

Figure 12:
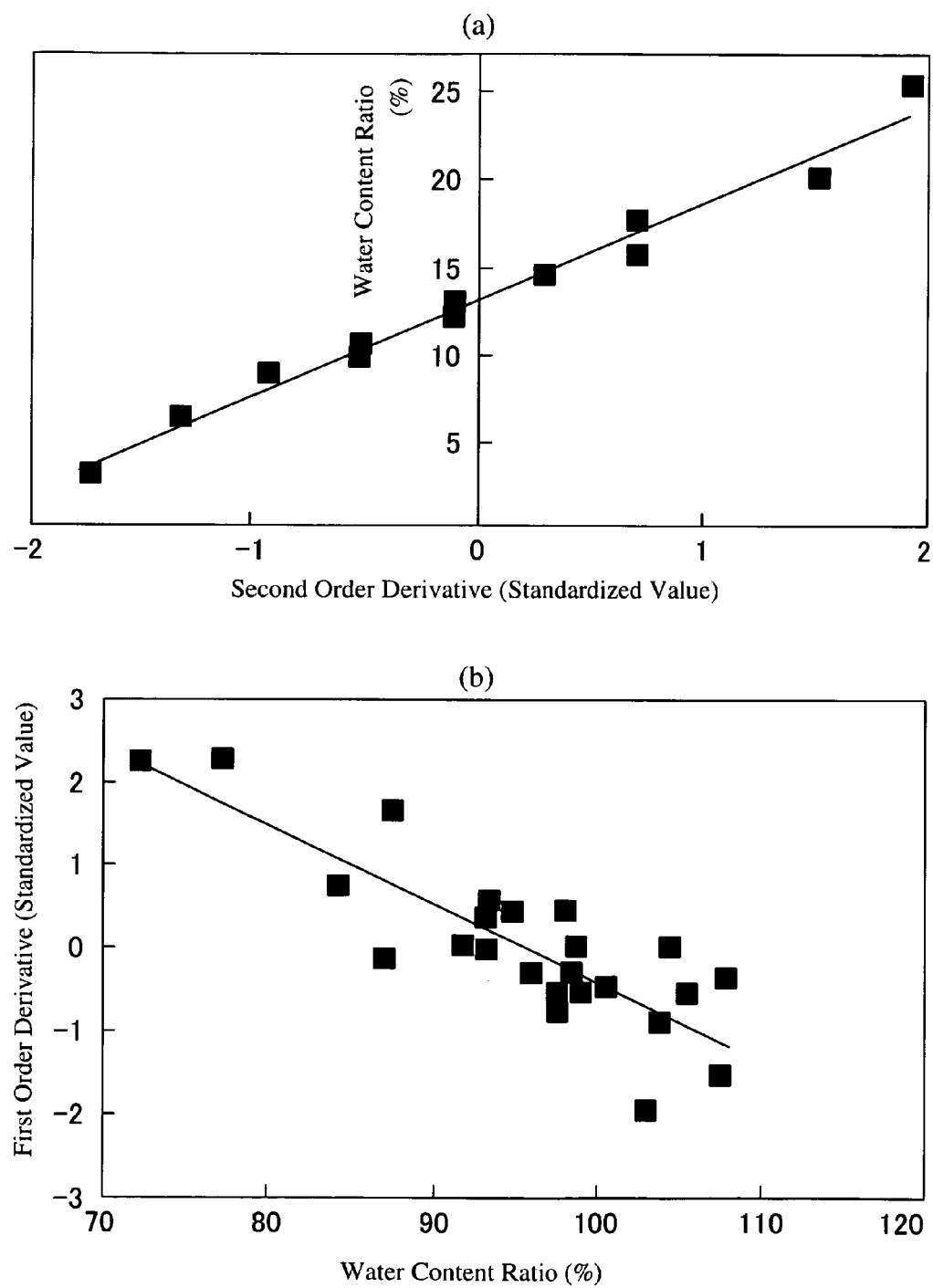
FIG. 12 is a graph demonstrating the accuracy of the accurate water content ratio model.

On the other hand, instead of a rough water content ratio, there are cases where the water content ratio needs to be known at a higher accuracy. Accordingly, in the case where the name of the measurement object property is the accurate water content ratio for upland field having a low water content ratio, calculations can be carried out by a model formed from a first-order expression like that shown in FIG. 10. However, as shown in the drawing, the quantity W which is calculated based on the measurement data X is the standardized value for the second-order derivative value Y. The standardized value is the same as that used when calculating the rough water content ratio by the water content ratio detecting portion 57. Further, the correlation between the standardized value of the second-order derivative and the water content ratio is like that shown in FIG. 12(a). As is clear from this drawing, the values lie roughly on a straight line, and the obtained results indicate that the coefficient of determination $R^2$ is 0.980.

In the same manner, in the case of upland field having a high water content ratio, the operation expression is the same as that for the above-described case where the water content ratio is low, and has the same point that only one wavelength is used. However, the specific values of the coefficients A, B and the wavelength 1,850 nm established as the measurement condition are different. Furthermore, the point that the standardized value of the first-order derivative of the quantity of reflected light is used is also different. Further, the correlation between the standardized value of the first-order derivative and the water content ratio is like that shown in FIG. 12(b). As is clear from this drawing, the values lie roughly on a straight line, and the obtained results indicate that the coefficient of determination $R^2$ is 0.706.

Further, with regards to electric conductivity, even though a graph showing a specific correlation is omitted from the drawings, the coefficients of determination $R^2$ would be 0.809 in the case of upland field having a low water content ratio, and the coefficients of determination $R^2$ would be 0.808 in the case of upland field having a high water content ratio.

Figure 13:
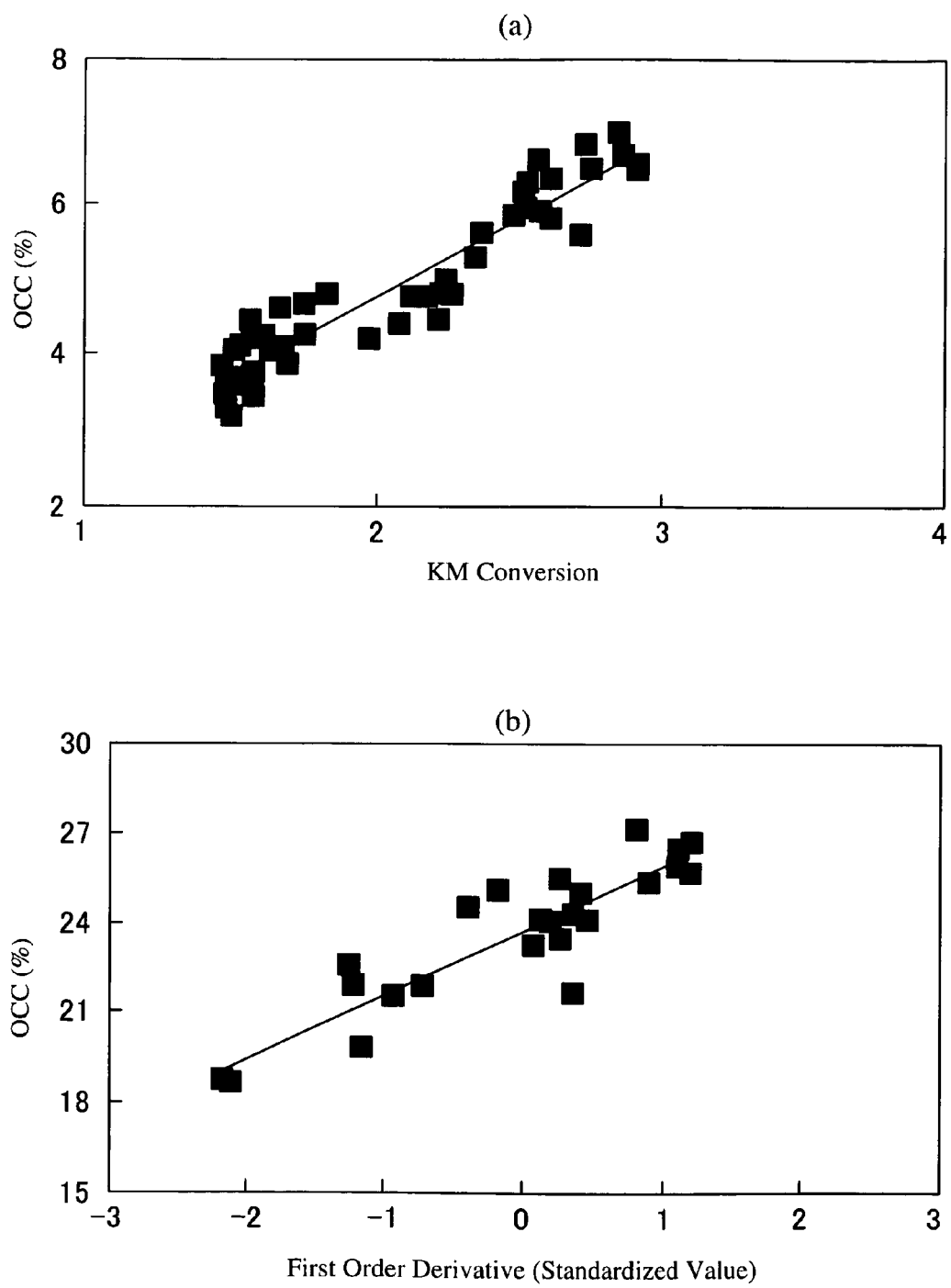
FIG. 13 is a graph demonstrating the accuracy of the organic matter model.

Moreover, in the case where the organic matter content is measured, measurement results like those shown in FIG. 13(a) are obtained, and the coefficients of determination $R^2$ is 0.886. Further, in the case of upland field having a high water content ratio, measurement results like those shown in FIG. 13(b) are obtained in the same manner, and the coefficients of determination $R^2$ is 0.811. In this way, correlation values having a high reliability can be obtained for any case.

Figure 14:
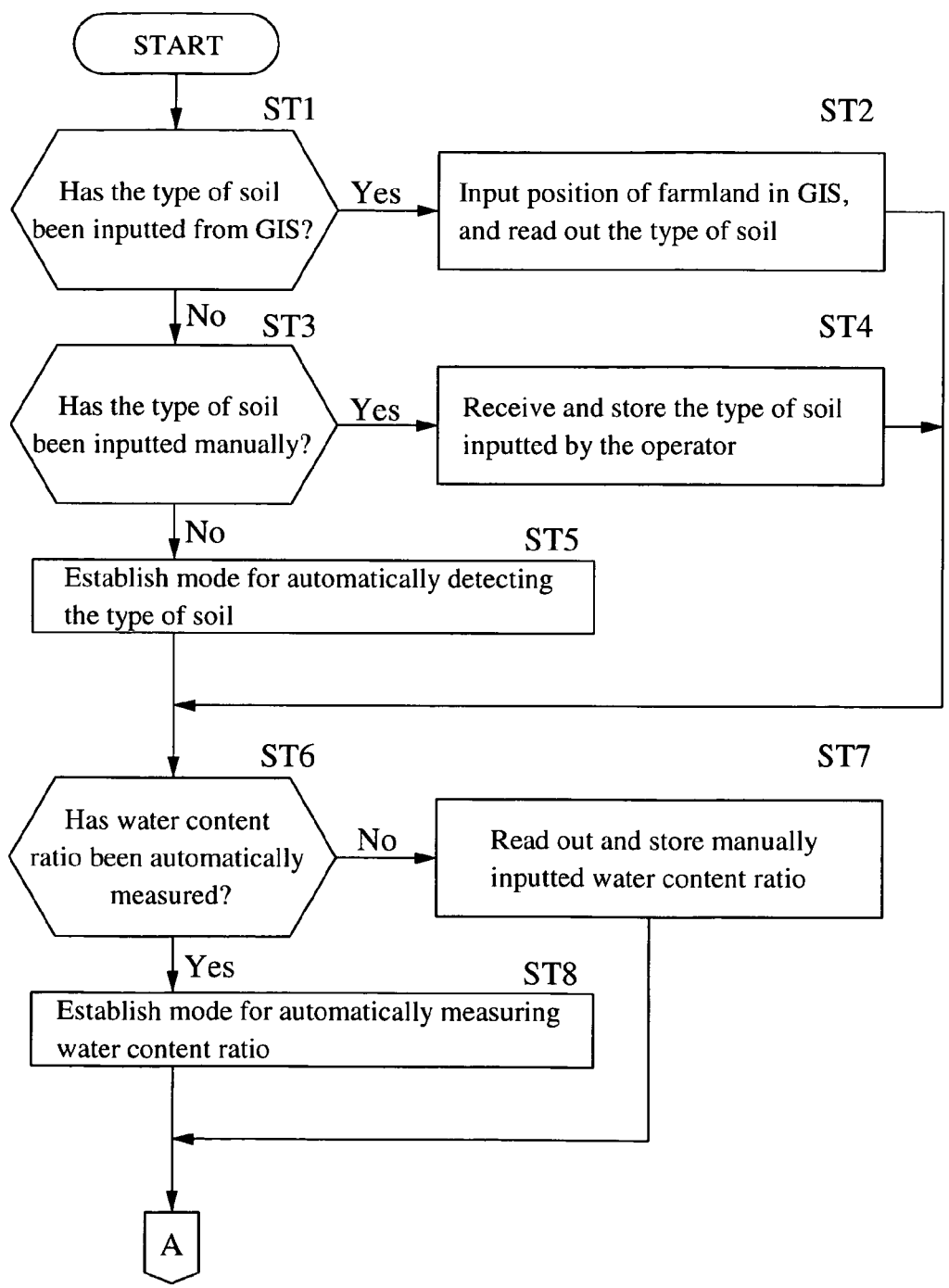
FIG. 14 is a portion of a flow chart showing the first embodiment of a soil measuring method and a soil measurement assisting method according to the present invention.
Figure 15:
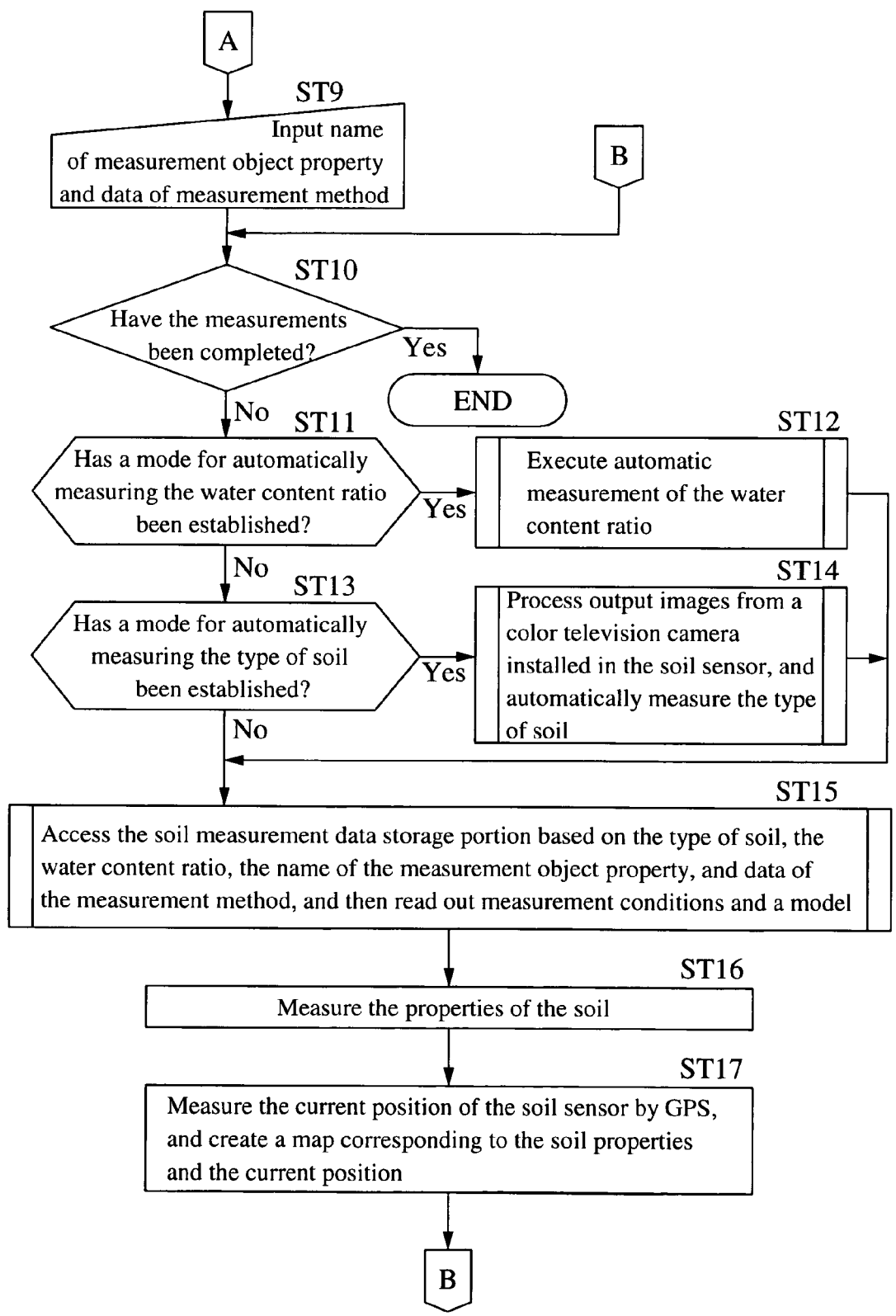
FIG. 15 is a portion of a flow chart showing the first embodiment of a soil measuring method and a soil measurement assisting method according to the present invention.

Next, a description will be given for one embodiment of a method of the present invention which uses the apparatus of the present embodiment described above. As shown in FIG. 14 and FIG. 15, first, a judgment of whether or not the type of soil has been inputted by GIS is carried out (ST1). Then, in the case of the mode for inputting from GIS, the process skips to Step 2, and the measured farmland position is inputted, and then based on this the GIS data storage portion 63 is accessed, and the type of soil stored in corresponding GIS data is read out. After that, the process proceeds to Step 6 (measurement mode judgment of the water content ratio).

On the other hand, in the case where there is no input from GIS ("No" at the branching judgment of Step 1), the process skips to Step 3, and a judgment of whether or not the type of soil will be inputted manually is carried out (ST3). Then, in the case where manual input is carried out, the process skips to Step 4, the type of soil inputted by an operator is received and stored. Further, in the case where manual input is not carried out, the process proceeds to Step 5 and a mode for automatically detecting the type of soil is established. Namely, based on the measurement data, the feature extracting portion 56 and the type-of-soil discriminating portion 58 are operated to judge the type of soil.

As described above, after the input mode (GIS/manual/automatic) of the type of soil has been determined, a judgment of whether or not the water content ratio will be measured automatically is carried out (ST6). Then, in the case where automatic measurements will not be carried out, the water content ratio inputted from the manual input portion 62 is read out and recorded (ST7). Further, in the case where measurement is automatically carried out, an automatic measurement mode is established (ST8). Namely, based on the measurement data, the water content ratio detecting portion 57 is operated to judge the water content ratio.

Next, the name of the measurement object property and the data of the measurement method supplied from the manual input portion 62 are received (ST9). Further, this process of Step 9 and the process described above for establishing the input mode of the type of soil and the input mode of the water content ratio do not need to be limited to the order described above, and it is possible to execute such processes in any order. Then, when each of the processes described above is completed, the process described below is carried out for each measurement point until measurements are completed (ST10).

First, judgments of whether or not the water content ratio and the type of soil are automatic measurement modes are carried out (ST11, ST13). In the case where they are not automatic measurement modes, because corresponding values are previously stored, such stored values are used. Further, in the case of automatic measurement modes, the water content ratio is calculated based on the quantity of reflected light (ST12), and the type of soil is established based on the color images that are taken (ST14).

When the processes up to Step 14 have been carried out as described above, because the four types of input data (type of soil, water content ratio, name of measurement object property, and measurement method) are established for the site to be measured, the determining portion 59 accesses the soil measurement data storage portion 60 based on such input data, and reads out corresponding measurement conditions and a model (ST16). Then, the measurement conditions are set in the soil sensor S, and the model is supplied to the measurement information processing portion 55.

After that, as the required measurement data established by the measurement conditions is supplied from the soil sensor S to the measurement information processing portion 55, the model based on such measurement data is utilized to measure the soil properties (ST16). Then, a map correlated with such calculated soil properties and position information (calculated by GPS) of the measurement site is created by the soil map creating portion 50 and stored in the soil map storage portion 52. The processes of Step 11 through Step 17 are repeated until measurements are completed (normally, when all the regions of the field have been measured).

Figure 16:
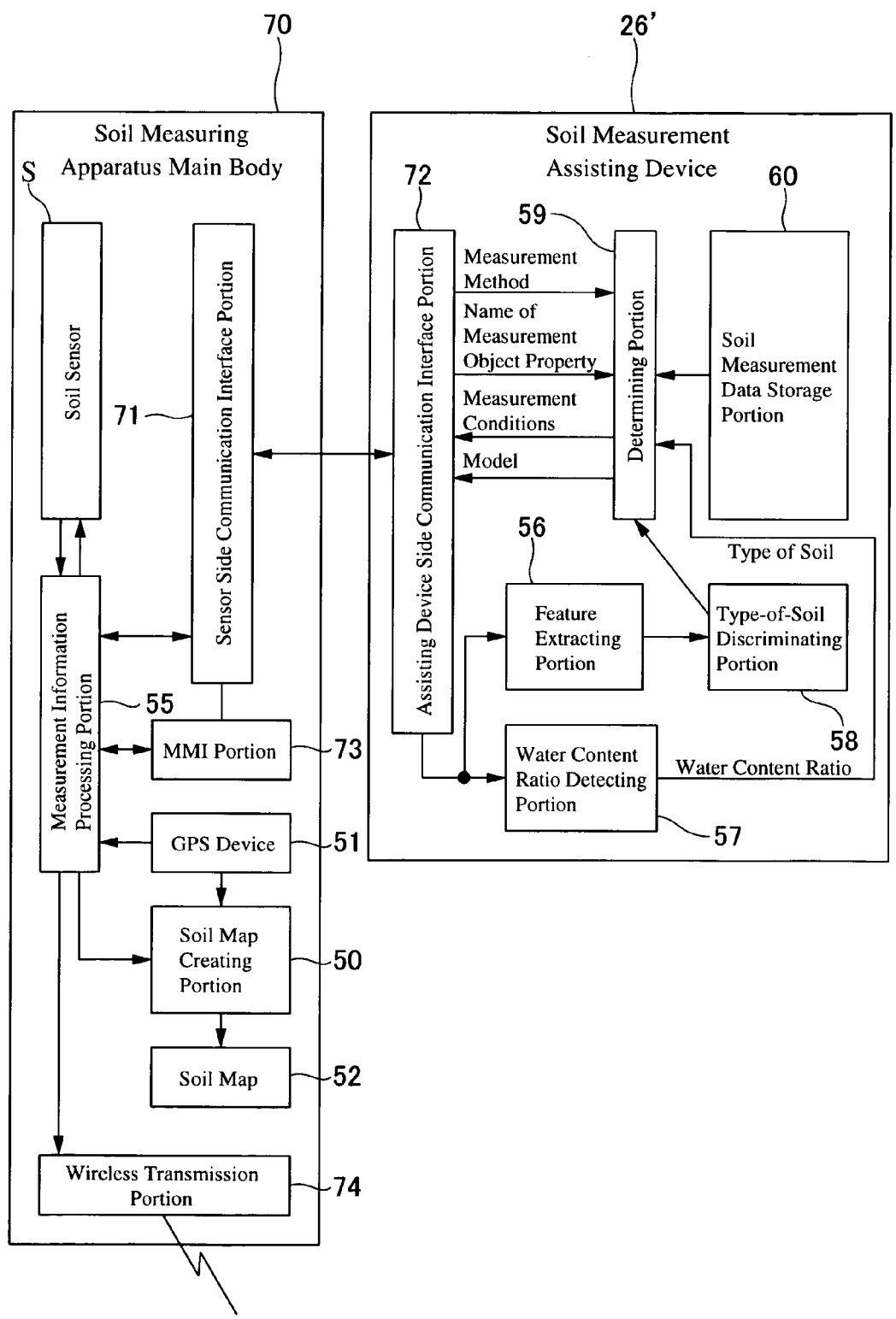
FIG. 16 is a block diagram showing the first embodiment of a soil measuring apparatus and a soil measurement assisting device according to the present invention.

FIG. 16 shows a second embodiment of the present invention. As shown in this drawing, the present embodiment is constructed from a soil measuring apparatus main body 70 which is mounted to a tractor or the like to move through a field, and a separately provided soil measurement assisting device 26' which communicates with the soil measuring apparatus main body 70 to establish measurement conditions and models, and which is not mounted to the tractor. Of course, when these are actually used, the soil measurement assisting device 26' may also be mounted to the tractor to move through the field together with the soil measuring apparatus main body 70. In short, the present embodiment may be formed by an apparatus main body which actually measures the soil properties, and a separately provided assisting device which establishes various conditions required for carrying out measurements.

Further, data is communicated between the soil measuring apparatus main body 70 and the soil measurement assisting device 26' via respectively provided communication interface portions 71, 72. This data communication can be carried out using any wire or wireless communication medium.

Further, as for the specific structure, in the apparatus structure shown in FIG. 6, the processing portion required at the time the soil properties are actually measured, namely, a soil sensor S which acquires various information from the soil surface, a measurement information processing portion 55 which measures the soil properties based on the measurement data supplied from the soil sensor S, a soil map creating portion 50 for creating soil maps based on the measurement results outputted from the measurement information processing portion 55, a GPS device 51 which acquires position information, a soil map storage portion 52 which stores soil maps created by the soil map creating portion 50 and the like are housed in the soil measuring apparatus main body 70.

Further, the soil measuring apparatus main body 70 is equipped with a man-machine interface portion 73 for supplying various control commands from an operator or the like to the measurement information processing portion 55, and a wireless transmitter portion 74 for transmitting the measurement results of the measurement information processing portion 55 to an outside device.

On the other hand, at the soil measurement assisting device 26' side, in the apparatus structure shown in FIG. 6, a process portion for executing a pre-process function, namely, a feature extracting portion 56 and a type-of-soil discriminating portion 58 for automatically calculating the type of soil, a water content ratio detecting portion 57 for automatically calculating the water content ratio, a soil measurement data storage portion 60, and a determining portion 59 for determining the measurement conditions and the like are provided. Further, although omitted from the drawing, it is of course possible to provide GIS data and the like.

Further, in the present embodiment, the measurement data required for automatically calculating the type of soil and the water content ratio are supplied from the soil sensor S via the measurement information processing portion 55 and from the measuring apparatus main body 70 via the communication interface portions 71, 72. Further, the manually inputted data such as the measurement method and the name of measurement object property and the like are also supplied from the soil measuring apparatus main body 70. Specifically, the data supplied from the man-machine interface portion 73 is supplied via the measurement information processing portion 55. Of course, it is also possible for such data to be supplied directly via the communication interface portion 71 instead of through the measurement information processing portion 55. Furthermore, even in the case where the type of soil and water content ratio are manually inputted, such information can be supplied to the determining portion 59 by the same route as that of the measurement method and the like described above.

Further, the measurement conditions and the model determined by the determining portion 59 are transmitted to the soil measuring apparatus main body 70 via both communication interface portions 71, 72, and are established in the soil sensor S via the measurement information processing portion 55. Namely, in the present embodiment, in addition to a function for measuring the essential soil properties, the measurement conditions establishing portion shown in FIG. 6 and a data transfer function are also added to the measurement information processing portion 55. Further, because the specific process functions of the other various processing portions are the same as those of the first embodiment described above, a detailed description thereof is omitted.

Figure 17:
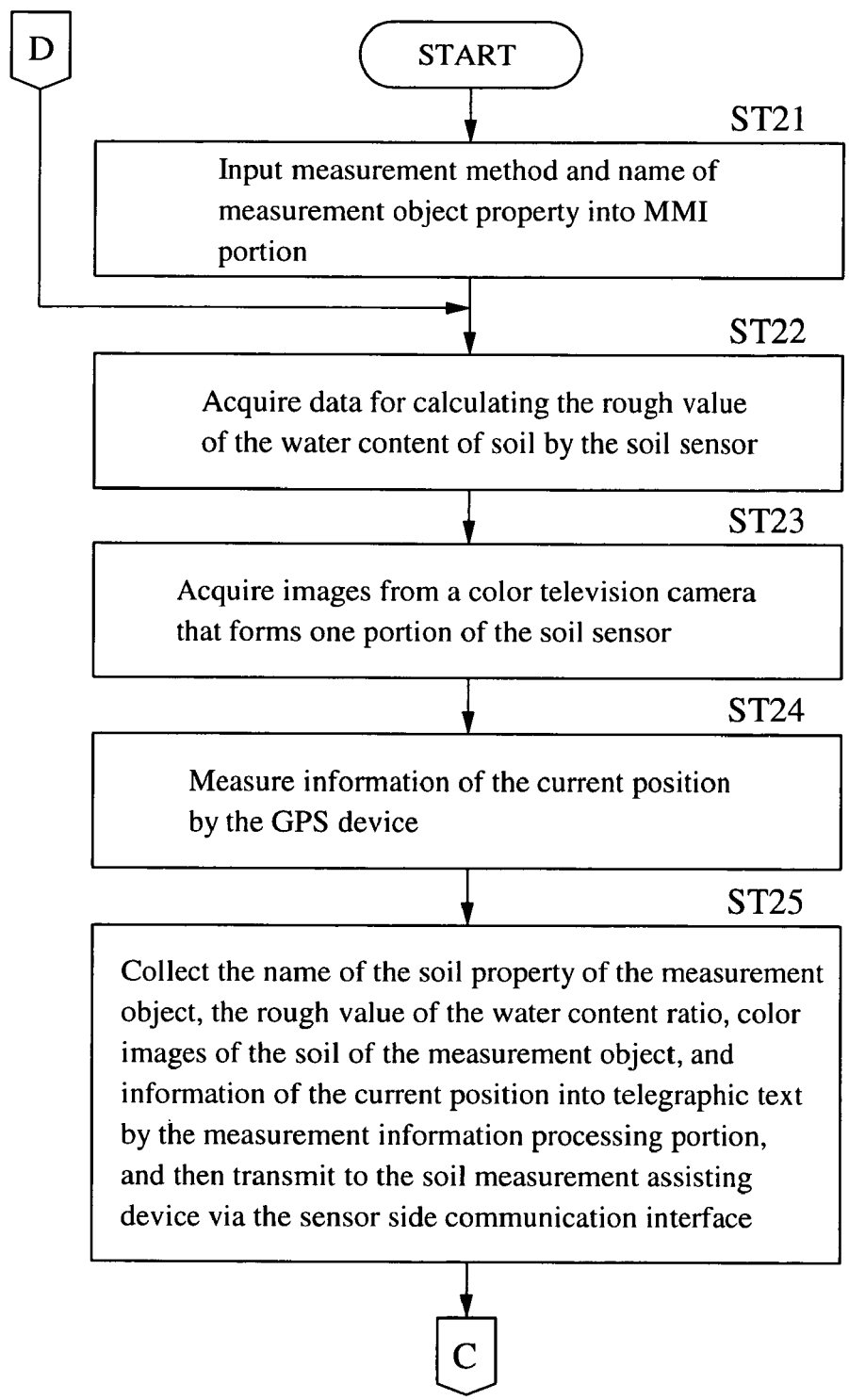
FIG. 17 is a portion of a flow chart showing the second embodiment of a soil measuring method according to the present invention.
Figure 18:
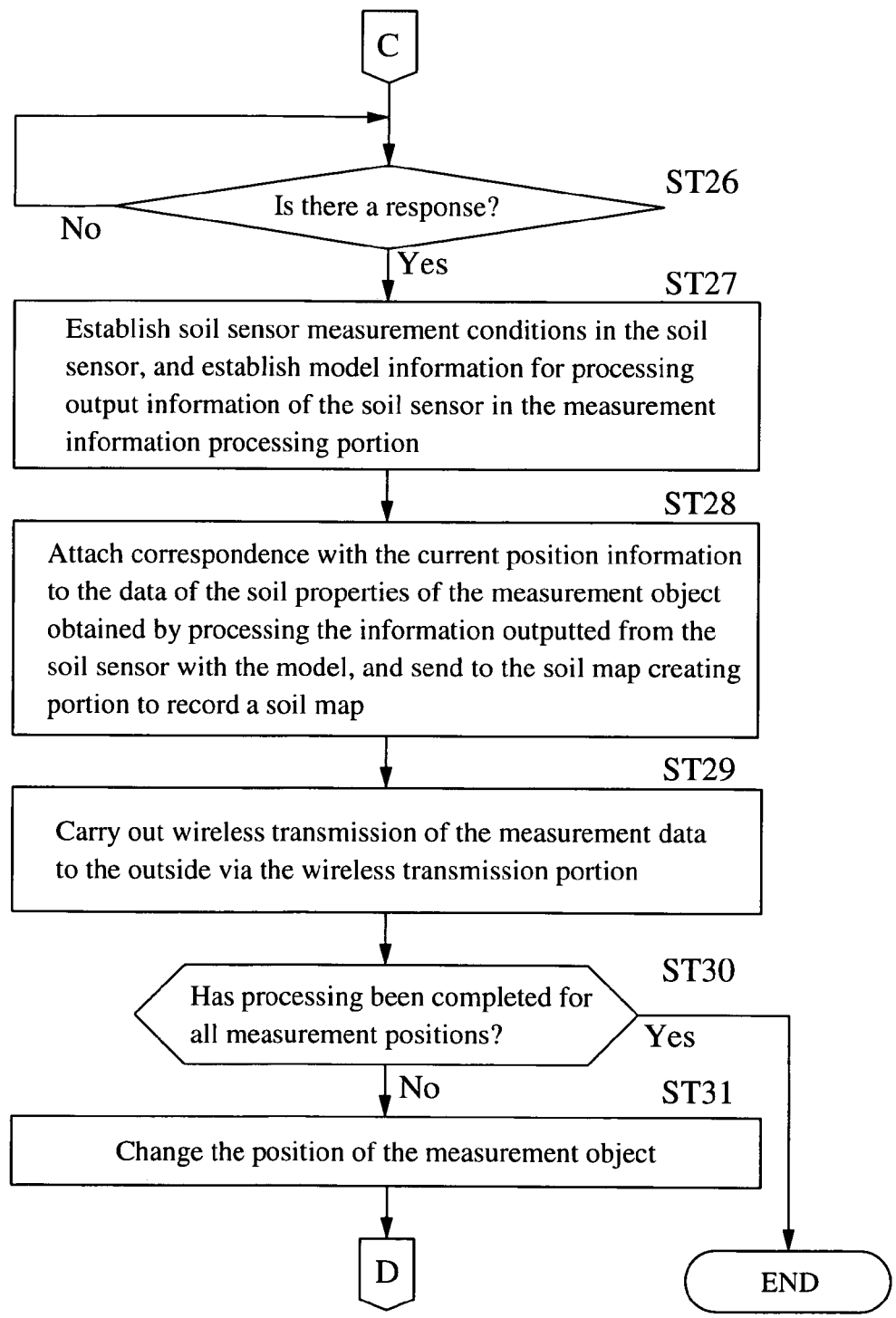
FIG. 18 is a portion of a flow chart showing the second embodiment of a soil measuring method according to the present invention.

Next, a description will be given for an embodiment of a measurement method according to the present invention which uses the apparatus of the second embodiment described above. FIG. 17 and FIG. 18 show the process function of the soil measuring apparatus main body 70. As shown in these drawings, first, the measurement method and the name of the measurement object property are inputted using the man-machine interface 73 (ST21). As a result, the measurement information processing portion 55 receives such two types of input data. Further, data for calculating the rough value of the water content ratio is acquired from the soil sensor (ST22). For example, this data may be the quantity of reflected light at a specific wavelength. Further, color images of the soil surface taken by a color television camera are acquired (ST23). Further, current position information is obtained using the GPS device 51 (ST24).

Then, the various types of information obtained by executing Steps 21~24 described above are collected into a telegraphic message by the measurement information processing portion 55, and sent to the soil assisting device side via the communication interface portion 71 at the sensor side (ST25). Further, in the case where the position information does not utilize GIS data, there is no particular need to carry out transmission in a collected telegraphic message.

The soil measurement assisting device acquires the various types of information sent by the telegraphic message and calculates the type of soil and water content ratio, and the determining portion 59 determines the measurement conditions and the model based on the type of soil and water content ratio information, and on the supplied measurement method and name of the measurement object property. Then, the determining portion 59 collects the measurement conditions and the model into a telegraphic message which is then transmitted to the soil measuring apparatus main body 70 via the communication interface portion 72 of the assisting device side.

The soil measuring apparatus main body 70 judges the presence or absence of a response sent from the soil measurement assisting device 26' (ST26), and when a response is received, the measurement conditions are established in the soil sensor S based on the received data, and the model is established in the measurement information processing portion 55 (ST27).

Then, the measurement information processing portion 55 receives measurement data outputted from the soil sensor S by the established measurement conditions, and calculates the soil properties based on the model. Then, a map having a correspondence with the position information detected by the GPS device 51 is created by the soil map creating portion 50 (ST28). Further, the calculated measurement information and the like can be transmitted to an outside portion via the wireless transmission portion (ST29). Then, the above-described series of processes are executed for all the measurement positions (ST30, 31).

Further, in the embodiments described above, the water content ratio is inputted manually or determined based on the quantity of reflected light, but the present invention is not limited to this arrangement, and it is also possible to calculate a rough value by a moisture sensor or the like. Furthermore, in each of the embodiments described above, a description was given for the case where the soil properties are calculated based on the quantity of reflected light, but the soil sensor is not limited to this arrangement, and it is also possible to carry out detection based on mechanical, electrical, chemical or other various information.

Figure 19:
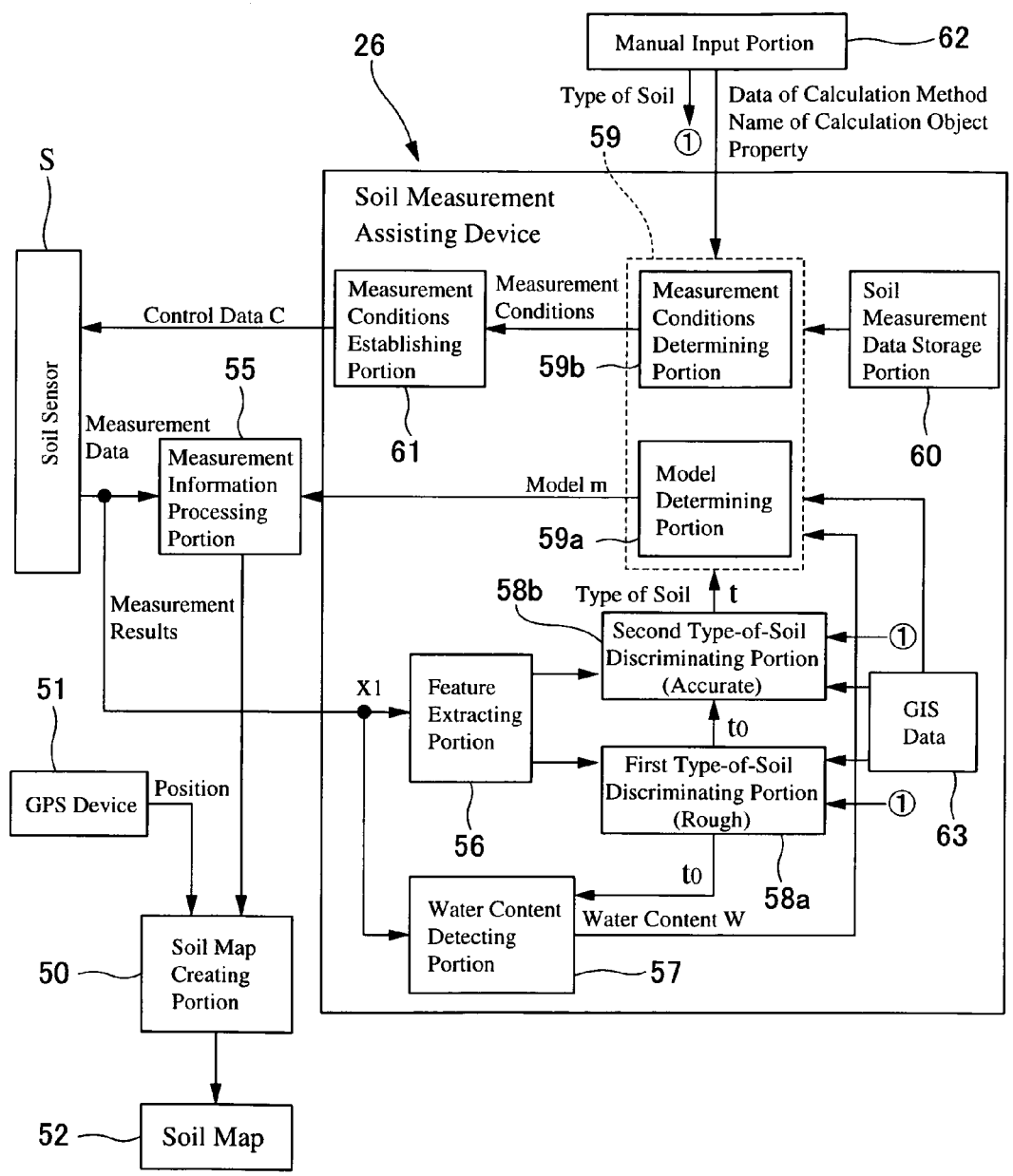
FIG. 19 is a block diagram showing another embodiment of a soil measuring apparatus and a soil measurement assisting device according to the present invention.

FIG. 19 shows another embodiment of the present invention. In the present embodiment, the soil measurement assisting device 26 is improved. Namely, in the soil measurement assisting device 26 in the present embodiment, the main difference is that the method of establishing the type of soil is changed. A description will be given regarding the types of soil. As for the types of soil, for example, there are an International Soil Institute method (soil classification by triangular diagram) and the farmland soil classification. The former carries out classification by the clay content, and the later carries out an overall judgment from the generated action and the like of the soil. Further, the specific details of such classifications are given below.

First, as shown in FIG. 20, the kinds of soil based on the International Soil Institute method are separated into three kinds defined as clay, silt and sand based on particle size. Then, the types of soil are first classified into four grades by the clay content, and are then classified into a total of 12 types according to the proportion of sand (or silt) (see FIG. 21).

Further, in order to accurately measure the proportions of clay, silt and sand, particle size analysis needs to be used in a laboratory, and because the clay content corresponds to EMI (Electro-Magnetic Induction), four main classifications (heavy clay type, clay type, clayey soil type, sandy soil type) can be discriminated by utilizing the EMI.

Further, the clay content is a parameter which affects the water retention and mechanical properties of the soil. Consequently, because the clay content is related strongly to the characteristics of the fertility parameter (nitrogen and the like), sufficient results are obtained even when only discriminating the four main classifications described above.

On the other hand, it is difficult to judge the type of soil based on the farmland soil classification when a data base for each field has not been separately created, but the rough properties can be discriminated from the color of the soil.

The correlation between the color of the soil and the soil is like that shown in FIG. 8, but in a changed perspective, the correlation between the contained substances and the color is like that shown in FIG. 22. Further, as shown in the drawing, the color of the soil makes it possible to roughly classify the type of soil from the contained components. This point is like that described using FIG. 8.

On the other hand, when determining the water content ratio required for determining a model supplied to the measurement information processing portion 55, it will be difficult to calculate the rough value of the water content ratio when the type of soil is not determined to a certain degree. Namely, in the example case of clay and sand, even when they both have the same water content ratio, because sand has a poorer water retention compared to clay, the absorbance will show a spectrum in which the sand has more water.

In this regard, in the present embodiment, as shown in FIG. 19, a first type-of-soil discriminating portion 58a for determining the rough type of soil required for calculating the water content, and a second type-of-soil discriminating portion 58b for calculating the detailed type of soil required for actually determining a model m are provided as means for determining the type of soil based on measurement data outputted from the soil sensor S. In this way, the output of the first type-of-soil discriminating portion 58a is supplied to a water content detecting portion 57', and the output of the second type-of-soil discriminating portion 58b is supplied to the determining portion 59. Namely, in terms of the relationship with the embodiment shown in FIG. 6, the second type-of-soil discriminating portion 58b corresponds to the type-of-soil discriminating portion 58.

Furthermore, in the present embodiment, instead of determining the type of soil automatically as described above, it is also possible to determine the type of soil based on previously calculated data. Namely, the input of the position of the farmland to be measured is received, and then based on that, the GIS data storage portion 63 is accessed, and the type of soil stored for corresponding GIS data is acquired. Further, the position information of the farmland may be directly inputted by a user, or the position information may be acquired from the GPS device 51. Further, the type of soil may be directly inputted by the user from the manual input portion 62. This GIS data and the method of inputting by keyed input carried out manually by the user can be applied to any of the first, second type-of-soil discriminating portions 58a, 58b.

Further, in addition to the means which measures the optical properties of the soil such as the spectrophotometer and the like, the soil sensor S may employ various elements such as an image pickup device such as a CCD camera or the like which takes images of the soil surface of the measurement object, a sensor which detects EMI and a load cell or the like which measures the pressure or the like.

Then, measurement data x1, which is information other than the water content w such as EMI or image data or the like, is supplied from the soil sensor S to the first type-of-soil discriminating portion 58a. To be exact, the measurement data x1 is supplied to the feature extracting portion 56, wherein the feature quantity required for carrying out discrimination by the first type-of-soil discriminating portion 58a is extracted.

Without using information of the water content w, the first type-of-soil discriminating portion 58a determines the rough types of soil t0 using the measurement data x1. Specifically, when the measurement data x1 is image data obtained by taking images of the soil surface with a television camera, the soil surface undergoes texture analysis, and a judgment is carried out based on such analysis.

Namely, when the clay content increases, the texture becomes fine. Further, when the clay content decreases and the proportion of sand increases, the texture becomes coarse. Further, it is also possible to use a Fourier power spectrum as the feature quantity that represents the texture. In the case where the texture is fine, a relatively large energy component remains dispersed at a location far from the origin, but in the case of coarse texture, the energy converges close to the origin.

In this regard, based on received image data, the feature extracting portion 56 calculates the Fourier power spectrum which forms the texture feature quantity that represents the coarseness of the texture, and then this spectrum is supplied to the first type-of-soil discriminating portion 58a.

Then, based on the received Fourier power spectrum, the first type-of-soil discriminating portion 58a creates the rough types of soil (the four classifications defined as heavy clay type, clay type, clayey soil type, sandy soil type) t0. Namely, because the order from the fine texture is "heavy clay type →clay type →clayey soil type →sandy soil type", by previously establishing a threshold value for classifying each region, and judging which region the Fourier power spectrum that corresponds to the acquired texture coarseness belongs to, it is possible to easily calculate the rough type of soil. Then, the types of soil t0 calculated in this way is supplied to the water content detecting portion 57' and the second type-of-soil discriminating portion 58b.

Further, in the case where the measurement data x1 is the EMI, the rough types of soil (the four classifications defined as heavy clay type, clay type, clayey soil type, sandy soil type) t0 may of course be created based on the intensities of the EMI. Namely, because the electric conductivity EC is known from the EMI, the clay content is calculated by substituting the EC value into the regression expression given below.

clay content=22.8+0.133 *EC* value

Then, it is possible to calculate the type of soil from the calculated clay content. Further, the regression expression described above is calculated from the following relational expression (where A is a constant):

*EC* value=*A*+salt concentration+clay content

Furthermore, because there is a large resistance for high clay contents, by using a load cell or the like as a soil sensor S, and moving the load cell in an inserted state in the soil, it is possible to measure the rough types of soil based on the load resistance received from the soil at such time.

On the other hand, the second type-of-soil discriminating portion 58b uses the measurement data x1 supplied from the sensor S (actually, the feature quantity extracted based on the sensor output) and the rough types of soil t0 determined by the first type-of-soil discriminating portion 58a to calculate an accurate type of soil t. Then, the color images of the soil and the light absorbance of the soil are used as the measurement data x1. Then, specifically, the process described below is executed.

First, the color of the soil from the color images (RGB) is converted into three types of information defined as brightness, saturation and hue. Next, with the brightness, saturation and hue forming an index, the soil is classified into four classifications c0 based on high organic matter soil, low organic matter soil, oxidization, and reduction soil color. Namely, from a standard soil color system, the range of soil colors of the four types described above is specified by brightness, saturation and hue. Accordingly, by judging which range of types the feature quantity obtained by color converting the RGB data obtained based on the measurement data into brightness, saturation and hue belongs to, the classification of the feature quantity among the four classifications c0 can be calculated.

Then, the accurate type of soil t is calculated based on the classifications c0 calculated as described above, and a classification t1 calculated by the first type-of-soil discriminating portion. In this regard, the types of soil can be classified into a total of 16 types by combining t0 (four types) and c0 (four types). For example, the type of soil t may be determined to be a "heavy clay type soil having a high organic matter content" or a "sandy type soil which is oxidized."

The water content detecting portion 57' uses the rough types of soil t0 calculated by the first type-of-soil discriminating portion 58a and the measurement data x1 (reflected light spectrum from the soil) supplied from the soil sensor S to measure the water content w (three rankings). Determination is carried out by w=h(x1, t0).

Namely, water absorbs light centered around the 1,450 nm wavelength of the near infrared region. Further the observation surface of the soil, where the reflected light spectrum is measured, is determined by a device and fixed. Accordingly, by comparing the intensity of reflected light or the light absorbance (absorbance=log (1/R)R: reflected light intensity) calculated from the reflected light intensity or reflection intensity at the 1,450 nm wavelength with for example, a wavelength of 1,300 nm which is not absorbed by water, it is possible to calculate the relative water content ratio of the soil.

In this regard, by preparing a table of the calculated correlation between the relative water content ratio calculated based on the reflected light spectrum x1 and the rough types of soil t0 calculated by the first type-of-soil discriminating portion 58a, it is possible to calculate the approximate absolute value of the water content ratio of the observation soil.

Further, when the surface of the soil is uneven, the reflection spectrum from the soil will be weak, and the light absorbance will be large. Then, even for the same type of soil, the observed soil surface is normally not necessarily uniform. In this regard, when determining the accurate type of soil, information on the unevenness of the soil surface may also be included in addition to the rough types of soil to described above and the light absorbance information. For example, except for observation data of sites that have a large unevenness, the effect of the unevenness of the soil can be compensated or the like. Further, the measurement of the unevenness of the soil can be carried out by shining a laser along a line from an oblique direction, whereby the depth of the unevenness can be measured by an optical cutting method.

Using the water content w calculated by the water content detecting portion 57' and the type of soil t calculated by the second type-of-soil discriminating portion 58b, the determining portion 59 accesses a soil model DB stored in the soil measurement data storage portion 60, and obtains the measurement conditions for controlling the soil observing apparatus and the soil measurement model m for calculating soil properties. Then, in accordance with the measurement conditions, the measurement conditions establishing portion 61 calculates control data C that will be supplied to the soil sensor S, and then supplies the calculated control data C to the soil sensor S.

The control data C and the soil measurement model m are read out from DBc and DBm, as shown below.

$$m = DBm(w, t)$$

$$C = DBc(w, t)$$

The control data C is supplied to the soil observing apparatus, specifically the soil sensor S to control the operating conditions of the sensor used for soil observations. The soil measurement model m is used as a parameter for processing observation data x obtained under the operating conditions established in this way. Namely, the soil measurement model m and the control data C correspond to the outputted "model" and "measurement conditions" shown in FIG. 6. Then, the output conditions corresponding to the water content (water content ratio) w that forms the input conditions and the types of soil t are retrieved and outputted. This process function in the determining portion 59 and the measurement conditions establishing portion 61 is the same as that of the embodiment shown in FIG. 6. Of course, when the method of classifying the types of soil is changed, the control data c and the soil model m stored in the soil measurement data storage portion 60 undergo corresponding changes. Further, strictly speaking, the soil model m and the control data C change depending on, for example, the soil temperature and weather conditions such as hot/cold weather and the like. Accordingly, temperature data is inputted automatically by a temperature sensor or directly inputted by a user using the manual input portion 62, and preferably the determining portion 59 also takes such weather conditions (temperature information) into account when determining the control data C and the soil model DB.

Then, when actual measurements are carried out, the measurement data outputted from the soil sensor S is supplied to the measurement information processing portion 55, and then the measurement information processing portion 55 carries out an arithmetic process in accordance with the model m supplied from the determining portion 59, and calculates the condition of the soil. Further, the calculated condition of the soil and position information obtained from the GPS device 51 are supplied to the soil map creating portion 50, and then a soil map is created therein and stored in the soil map storage portion 52. Now, because these processes in each portion can use the same processes as those of the embodiment shown in FIG. 6, a detailed description thereof is omitted.

Next, a description will be given regarding the method of creating a soil model m for a new soil. In the case where a soil model for the same location or a different location (having the same type of soil) has been previously created and stored in the soil measurement data storage portion 60, as described above, by reading out the corresponding soil model from the determining portion 59, it is possible to accurately measure soil properties in real time.

Figure 23:
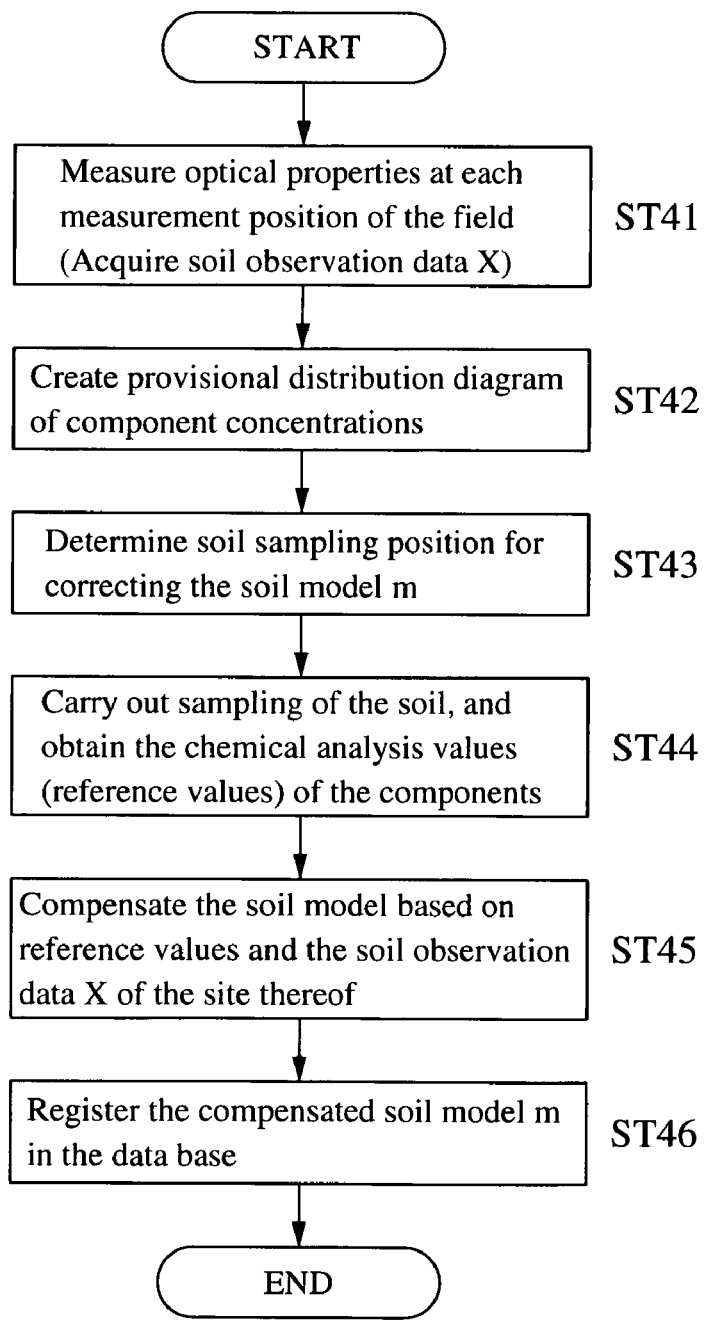
FIG. 23 is a flow chart that compensates a soil model.

However, in the case of a completely new field, or the same field having a changed type of soil due to some primary cause, there are cases where the data base of previously created types of soil can not have an accurate correspondence. In such case, when the soil properties are different, the regression expression (analytical curve) for component calculation needs to be compensated using the chemical analysis values of the soil. In this case, the method of creating a soil model m for a new soil can be executed, for example, according to the flow chart shown in FIG. 23.

First, the optical properties (soil light spectrum) of each site of the field for which a soil model m is to be created is measured (ST41). Then, a previous model expression (soil measurement model m) for calculating the component concentrations in the obtained soil light spectrum (observation data X) is applied, and a provisional distribution diagram of the component concentrations is created (ST42). As for the model that is used here, in the case where the rough type of soil of the measured field is estimated, a model expression for a soil that is close to such type of soil is utilized. Further, when a general purpose model expression can be established, it is possible to utilize such expression.

Next, a soil sampling position for obtaining the actual measured component values (reference values) for correcting the soil model m is determined (ST43). Specifically, the provisional distribution diagram (soil properties map MAP (R)) of the components calculated at Step 42 is referred to, and a position for sampling the soil so that the component concentration is uniformly distributed is determined by such provisional distribution diagram.

Next, soil at the soil sampling position determined at Step 43 is sampled, and the chemical analysis values (reference values) of the actual components are obtained (ST44). Then, using the reference values for each soil sampling position and the soil observation data X which forms the actual measured values, the soil model m used when creating the provisional component concentrations at Step 42 is compensated from such discrepancies (ST45).

Thereafter, the compensated soil model m is recorded as the soil model m in the soil measurement data storage portion 60 (ST46). Further, by using this compensated soil model m to calculate the component concentration distribution from the observation data X calculated at Step 1, it is possible to create a distribution diagram at the point in time of such measurements. Furthermore, this method is not limited to model determination for new soils, and it is possible for such method to be applied for improving the accuracy of a previous soil properties map MAP (R).

Figure 24:
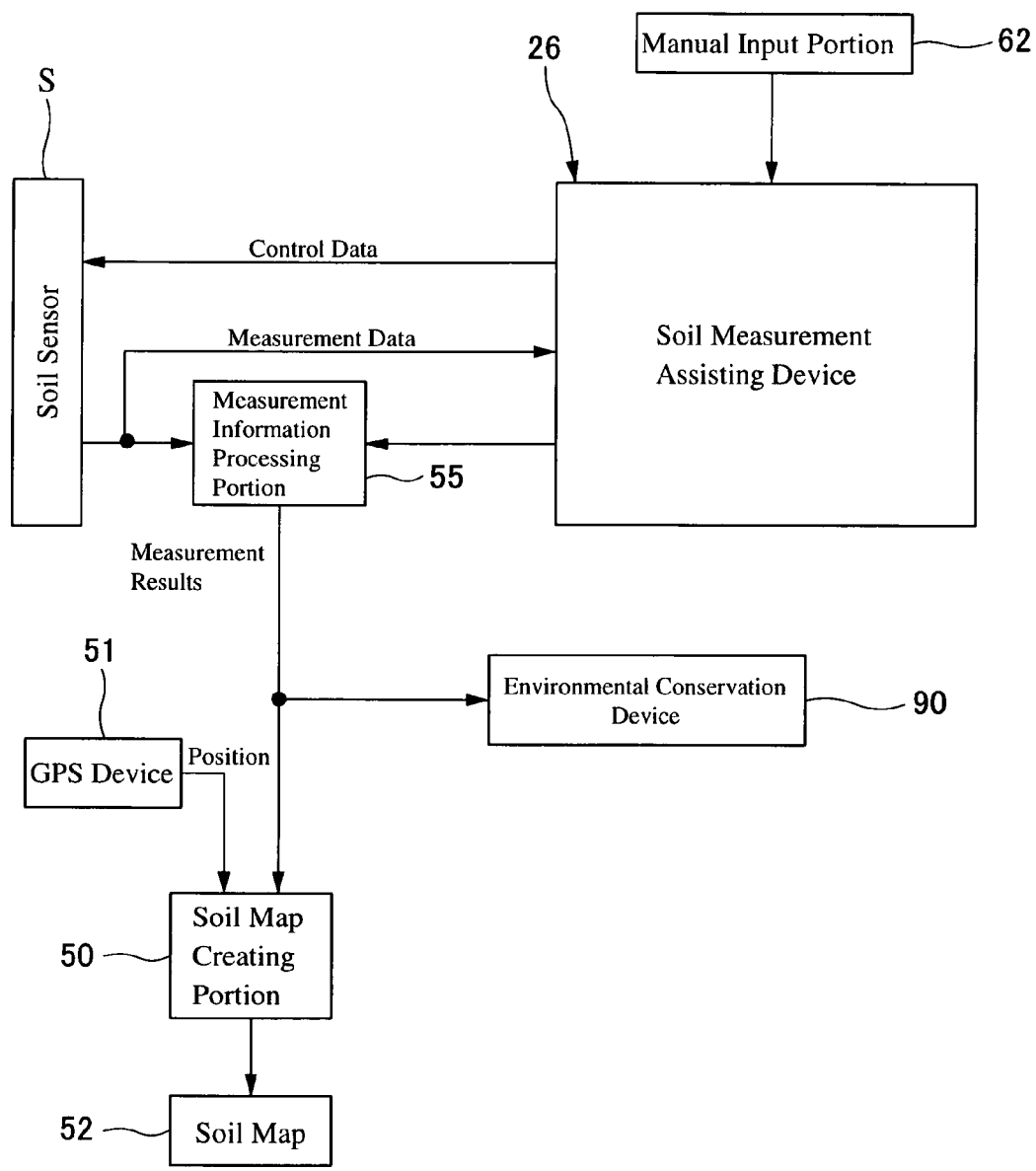
FIG. 24 is a block diagram showing another embodiment of the present invention, and is a drawing that shows an embodiment which includes an environmental preserving device.

FIG. 24 shows another embodiment of the present invention. In the present embodiment, the apparatus shown in FIG. 19 is used as a base, and an environmental conservation device 90 is provided. This environmental conservation device 90 is a device which carries out farm working of the type where the environment is considered at the site based on a soil property value f calculated by the measurement information processing portion 55. The execution of this environment consideration type farm working or the device which carries out such execution is referred to as a sensor base PF.

Namely, in the present embodiment, when sensing is carried out on a soil, the condition of the soil such as the soil components or the like at the site undergoing sensing can be calculated in real time. Accordingly, for example, when a fertilizer is applied, it is possible to calculate the optimum amount of applied fertilizer, and this makes it possible to preemptively prevent environmental pollution of the soil caused by supplying the fertilizer above the required amount and the generation of adverse effects on agricultural products due to overfertilization. Further, the condition of the soil after the fertilizer is applied can be easily calculated from the current condition of the soil and the amount of applied fertilizer. Accordingly, it is possible to know whether or not the condition of the soil after application lies within a range permitted by an environmental standard before the fertilizer is applied. Accordingly, it is possible to preserve the environment by controlling the application amount so that it always falls under the environmental standard. In other words, it is possible to accurately carry out quality control of the farm working.

Of course, the farm working that forms the subject is not limited to the application of fertilizers, and it goes without saying that environmental preservation can be applied to various kinds of farm working. Furthermore, in the case where the soil environment has deteriorated, various processes for improving such state are carried out, and these can be started immediately after measurements, whereby it becomes possible to keep damage to the soil, agricultural products and environment to a minimum.

The environmental conservation device 90 determines required operation contents based on the process described above, namely, the measurement results outputted from the measurement information processing portion 55, and automatically executes the determined operation contents.

For example, in the case where the operation content is fertilizer application, the fertilizer application amount z at such site can be determined by the following expression. Further, the device may include a function to actually apply a corresponding fertilizer in accordance with the determined fertilizer application amount z.

$z=\alpha(Ym-y)$: when Ym−y is positive

0: when Ym−y is non-positive

In this regard, Ym is a target value which corresponds to the soil property value y. Further, $\alpha$ is a function that converts Ym−y to the fertilizer application amount. At this time, by establishing Ym below a maximum value permitted by an environmental standard, the soil property value y at the site is established so as to not exceed the environmental standard. Further, specific fertilizers and agricultural chemicals will concentrate in specific places due to the effect of the flow of groundwater under the ground of the farmland and the like, and in order to prevent the environmental standard from being exceeded at such concentrated sites, the function $\alpha$ may be established so that it is possible to output the actual application amount z on the low side in view of safety in accordance with the properties of the farmland.

Figure 25:
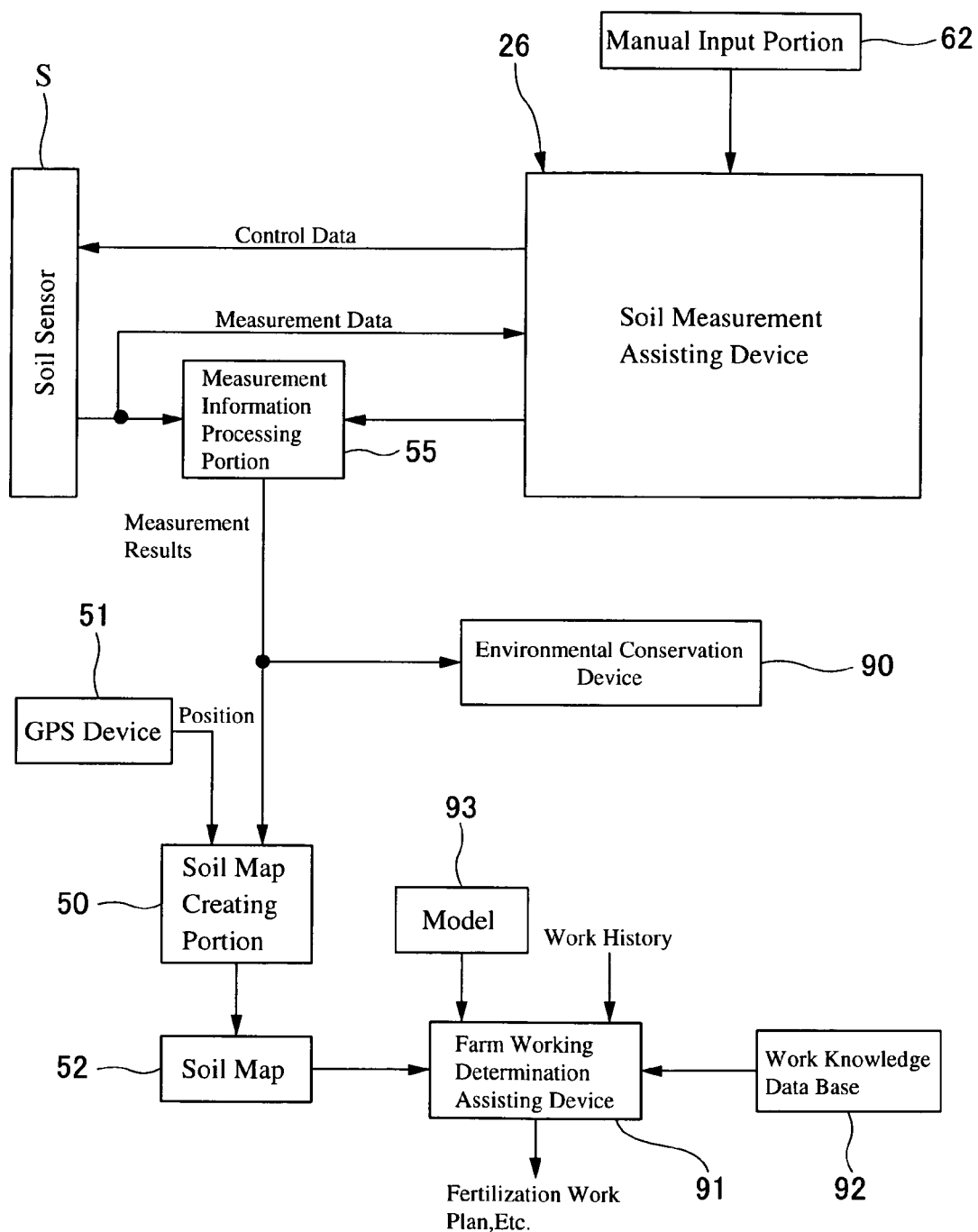
FIG. 25 is a block diagram showing another embodiment of the present invention, and is a drawing that shows an embodiment which includes a farm working determination assisting device.

FIG. 25 shows another embodiment of the present invention. In the present embodiment, each of the embodiments described above is used as a base in a farm working determination assisting system which determines a guide of what kind of farm working should be carried out at the present time or in the future based on the calculated soil map.

As shown in the drawing, information of the soil map (farmland map): MAP (R) stored in the soil map storage portion 52 and a work history (a history or the like of the agricultural application work and the fertilization work of each farmland) are supplied to a farm working determination assisting device 91. The work history can be inputted by a user using an input device such as a keyboard or the like. Further, in the case where the environmental conservation device 90 is included as shown in FIG. 24, by carrying out operations together with this, the actual work carried out by the environmental conservation device 90 may be automatically inputted.

The farm working determination assisting device 91 determines the farm working that should be carried out in the future, such as the fertilization work plan and the like, based on the received work history and soil map, information stored in a work knowledge data base 92, and various models 93, and then outputs the determined farm working.

The work information data base 92 stores information related to the farm working method required for determining the farm working, and is an information base that provides information in accordance with a request. Further, a function is included for renewing the read in contents of required information from a network, a recording medium or the like. Further, the work information base 92 includes information related to the breed of crops required for determining the farm working. These include the breed properties information such as the crop name, breed name, germinating rate, planting quantity, growth function, the flowering, the fructification function, the resistance to disease damage insects and the like, fertilization responsivity, environmental responsivity meaning the behavior to air temperature, sunlight and the like, cultivation workability which shows the important points of the cultivation work, cultivation properties formed from the harvesting method and the like, storage/transportation properties such as ripeness, aging, density, volume, the shape and like, and the like. Further, the information related to the fertilizers is formed from the cost, effects, components, application method and the like. The information related to the agricultural chemicals is formed from the cost, effects, components, application method and the like.

On the other hand, the models 93 include a growth model, a disease damage model, a weather model and the like. The growth model is a model for predicting the growth of the crop in agricultural units, and if a description of rice is given as an example, the model predicts the stalk number, grain producing period, maturation period, stalk length, grain length, grain number and the like. Further, the growth model also stores information on the actual results of crop growth from the start of predictions to the present point in time for each farmland. The disease damage model calculates the occurrence probability of disease, disease damage insects, and weeds in agricultural units. Further, after the occurring of the disease, disease damage insects, and weeds the model predict the spread of them and calculate the predicted damage. In this regard, the term "damage" refers to the percentage of the crop that cannot be shipped due to disease, disease insects, and weeds. Further, the disease model stores the actual occurrence results of previous causes and extents of diseases and weeds for each farmland.

The weather model is a model for predicting the weather in agricultural units. The weather model acquires local weather information of the region restricted to the surroundings of the farmland and wide-area weather information for a wider area, and outputs daily weather predictions of the air temperature, sunlight hours, rainfall amount and the like, and monthly weather predictions for the field.

The farm working determination assisting device 91 calculates proposals of an agricultural chemical application work plan and a fertilization work plan at the present time to achieve a maximum harvest from weather information from the weather model, information showing the prediction of the crop growth from the growth model, information showing the soil condition from the soil map, and work history information and the like. Further, as for the specific functional structure of the system that includes the farm working determination assisting device 91, it is possible, for example, to use the structure disclosed in Japanese Laid-Open Patent Report No. HEI 11-313594.

Further, in the example shown the drawing, the system that includes the farm working determination assisting device 91 was shown as being internally provided in the soil measuring apparatus in an integrated state with the soil measurement assisting device 26 and the like, but this farm working determination assisting device (map base PF) 91 portion may be made independent and kept at the server side.

Namely, while actually observing the soil at the farmland with the soil observation apparatus, the set comprised of the soil property value y determined by y=f (m, x) calculated by the measurement information processing portion 55, and the position R of the soil observing apparatus (GPS device 51) at such time may be transmitted to the server each time, with the soil map being created at the server side, or the soil map created by the soil map creating portion 50 may be transmitted collectively to the server.

In the farm working determination assisting device 91 of the server side, the soil map is used to create a work plan based on the work information base 92, the work history and the models 93. The algorithm which creates this work plan is the same as that described above. Further, the work plan created in this way is transmitted to a farm worker via a network or the like.

Furthermore, when the data from each field is centrally controlled by the server in this way, by having the farm worker who receives the supplied work plan supply the server side with data such as the crop yield, amount of consumed fertilizers and agricultural chemicals and the like which forms the results of the work that depends on the work plan, the results given below will occur.

Namely, at the server side, it is possible to carry out a judgment of whether the farm working contents determined by itself are optimum or not from the crop yield and the like. Further, the crop yield and the amount of consumed fertilizers and agricultural chemicals and the like can be stored as a work history together with soil map data in the server, and then this information can be utilized to output a work plan in accordance with inquiries from other fields and farms. Further, when work histories of a plurality of fields are recorded over a long period of time, the item having a high overall evaluation of the crop yield and amount of consumed fertilizers and the like can be selected from a previous work history related to another field which has map data similar to the inputted soil map data, and which has similar models (growth model, disease damage model, weather model), and this item can be used to create a work plan, whereby the reliability will be improved.

Further, when a work plan is determined from a plurality of samples, by creating a plurality of work plan proposals, and providing the farm worker with the crop yield, amount of consumed fertilizers and the like of each proposal, it is possible to widen the choices of the farm worker. Further, the causal relationship principle between the farm working and the soil map can be inductively calculated, and this makes it possible to design an advanced work plan.

Figure 26:
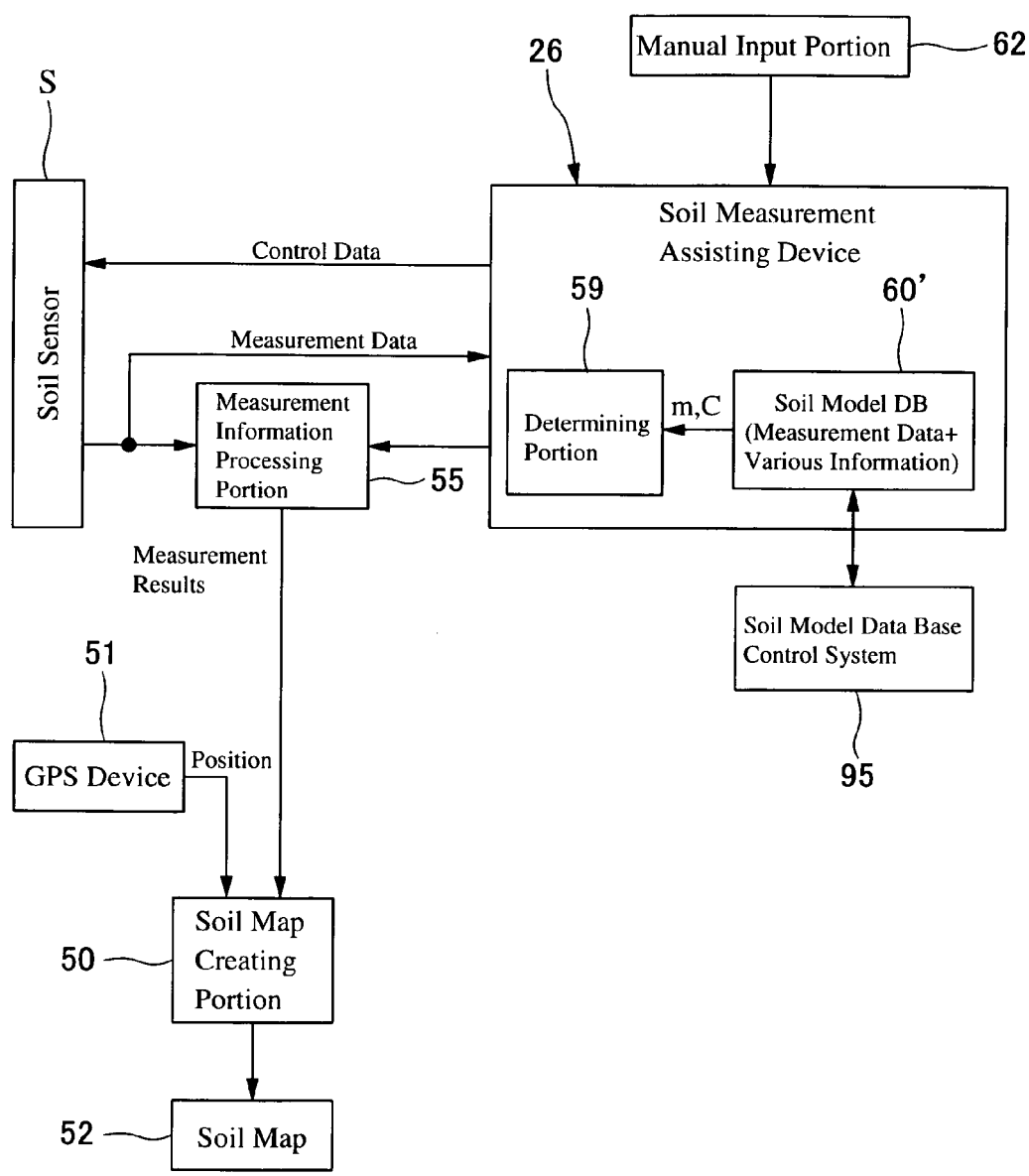
FIG. 26 is a drawing showing another embodiment of the present invention.

FIG. 26 shows another embodiment. In the present embodiment, a soil model data base 60' is provided in place of the soil measurement data storage portion 60 in each of the embodiments described above.

While the (1) soil model m and the (2) measurement conditions C formed the information held by the soil measurement data storage portion 60, in the soil model data base 60' of the present embodiment, other various information is correlated and stored in addition to such soil model and measurement conditions (control data) C. Further, an example of the internal data structure of this soil model data base 60' is shown in FIG. 27.

Namely, soil measurement information (m, C) correlated with the type of soil and the water content (as well as the name of the measurement object property and weather conditions), and soil correlation information are stored in a state that enables output so that such data can be read out by a computer. Further, examples of soil correlation information include advertisement information, the cultivation recipe, the actual harvest results, the location of the farmland, soil preparation directions information, and the like. Each of such information is stored in correlation with the type of soil and the water content. Further, a description of each information is as follows below. Further, as was described for the embodiment based on FIG. 19 described above, the weather conditions information is information used for measuring the condition of the soil at a higher accuracy based on the weather conditions (temperature information).

Advertisement Information

In accordance with the type of soil, the advertisement information includes advertisement of the crop seeds, agricultural chemicals, fertilizers and the like suited to farming with such type of soil, information on the advertisement of soil judgment services like those which judge whether or not the farmland can be advertised as using an "organic farming method" for example, and contamination information on contaminants (groundwater contaminants such as nitrate nitrogen, dioxin contaminants and the like) and information on services that analyze and evaluate such contamination information, and the like. The addresses and contents of such services are stored.

Information on Cultivation Recipe+Presentation of Actual Harvest Results

In accordance with the type of soil, the information on the cultivation recipe+the presentation of actual harvest results is information on the kinds of crops grown and the kinds of farm working used therefor, and the actual results of the kind of harvest that is obtained.

Farmland Location Information

The farmland location information is information mentioning where the farmland having the indicated type of soil is located, who the owner is, and where the address is. This information can be utilized by seed companies, agricultural chemical makers, fertilizer makers and the like to actively sell their own company's products to a user.

Soil Preparation Directions Information

The soil preparation directions information is the home pages of correspondence education which give directions for soil preparation classified by type of soil, and proposed pages of education material that give soil preparation directions. Further, the soil preparation directions information also includes information related to standards and countermeasures (optimum fertilization control model) and the like for preventing ground water contamination, topsoil erosion contamination and the like.

Now, as understood from the descriptions given above, various information is not used directly for carrying out actual soil measurements. Namely, from the data stored in the soil model data base 60', the soil model m and the measurement conditions (control data) C are supplied to the determining portion 59 inside the soil measurement assisting device 26.

On the other hand, other various information is used, for example, to access the soil model data base 60' based on the soil components calculated by the measurement information processing portion 55 and the type of soil of the field 10 calculated by various type-of-soil discriminating portions 58, 58a, 58b in order to read out relevant information which is then outputted to an output device such as a monitor or the like omitted from the drawings. In this way, because the user who uses the soil measurement assisting device 26 to measure the condition of the soil can know useful information related to one's own field, such arrangement is preferred.

Further, although omitted from the drawings, a search process for the soil model data base 60' described above and a functional processing portion which displays such search results need to be separately provided inside or outside the soil measurement assisting device 26. Further, instead of carrying out a search automatically, a function may be provided to enable the user to carry out a search manually.

The data stored in the soil model data base 60' described above can be utilized by obtaining a recording medium such as a CD-ROM, DVD or the like on which such data is recorded, reading out such data by a computer (soil measurement assisting device 26), and then storing such data in the storage portion inside the computer. Further, a drive device such as a CD-ROM drive or the like which reads data into a recording medium may be prepared, and then by setting a recording medium into the drive device, various information can be read onto the recording medium inside the drive device at such time.

Furthermore, it is also possible to acquire the above-described data transmitted via the Internet or another network. In this case, as shown in FIG. 26 for example, a soil model data base control system 95 which controls data that should be stored in the soil model data base 60' may be prepared, and by having the soil measurement assisting device 26 cooperate with the soil model data base control system 95, the data to be stored in the soil model data base may be obtained via the soil model data base control system 95.

At this time, because the soil model data base control system 95 is a computer of a tool device or the like, by making a connection with this computer via a cable or other communication medium (having wire/wireless capabilities), it is possible to carry out the transmission and reception of information. Further, by making a connection via the Internet or another network to carry out network transmission or the like, the required information can be acquired and stored in the soil model data base 60'.

In particular, in the latter case of network transmission, the newest information (any information of the soil model m, the measurement conditions (control data) C, and various information) can be easily acquired, and this makes it possible to expect the acquisition of highly accurate soil measurements and associated useful information. Further, the acquired information is not limited to the information stored in the soil model data base, and it is possible, for example, to supply a work knowledge data base and model required at the time the farm working determination assisting system is executed, as well as a determination algorithm (engine) or the like of the farm working determination assisting device 91.

Figure 28:
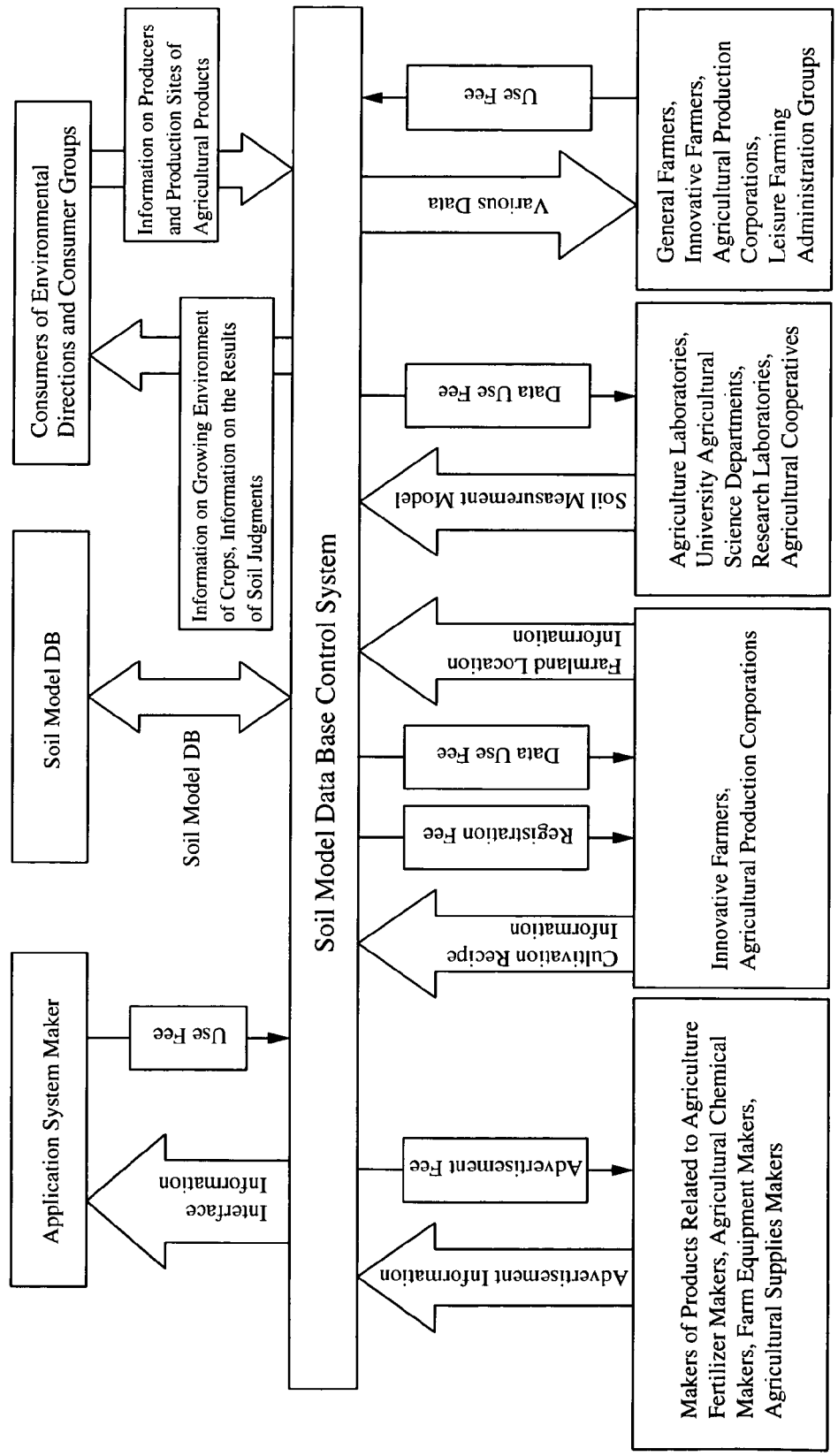
FIG. 28 is a drawing showing an example of a network system which includes a soil model data base management system.

FIG. 28 shows another embodiment of the present invention. In the present embodiment, the function of the soil model data base control system 95 is expanded, and it is possible for various users to connect with the soil model data base control system 95 via a network or the like in order to supply or receive information related to the soil model.

Further, examples of users (participants) who participate in the network centered around the soil model data base control system 95 are shown below. Further, these users are normally not connected at the same time, the soil model is utilized individually as needed via the network.

Operator

The operator is the person who controls and operates the soil model data base. This includes the person who has jurisdiction over the soil model data base control system 95.

Advertisers (Agricultural Product Makers)

The advertisers are the parties that submit advertisement information of their company's products to the data base to supply advertisements responding to the needs of persons accessing the data base in order to improve sales of their company's products. In actuality, when an advertisement fee is paid, the advertiser is registered in the column of the advertisement information corresponding to the types of soil in the soil model data base. This advertisement fee is paid to the operator who is also the system controller. For example, for a maker that produces and sells seeds or fertilizers, because related advertisement information is registered in the column of the type of soil suited for using such seeds or the like, and because such advertisement information will be frequently seen by persons needing such information, the commercial advertisement will be highly effective with good efficiency. Namely, the people who see the advertisement information, in many cases, people having a connection with such type of soil are, for example, "farmers and the like for whom the type of soil related to the advertisement information is the type of soil of their own field." Accordingly, for the advertisers, this forms a system having a high utility value.

Registrants of Cultivation Recipes and the like (Innovative Farmers, Agricultural Production Corporations):

The registrants of cultivation recipes and the like are the parties that create cultivation recipes of crops and actual harvest results data in accordance with the type of soil and the weather conditions, register such information in the soil model data base by paying registration fees, and receive data use payments in accordance with the number of times their own cultivation recipes are utilized. The method of settling money is not limited to the manner described above, and by having there be no registration fee, a reverse arrangement is possible in which money is received from the operator as an information supplying fee. In particular, because the important thing for the operator is that a significant amount of information be abundantly arranged by accurately and quickly collecting a large amount of information that is then registered in the data base, the information supplier (registrant) may pay no registration fee or may receive uniform payment of fees from the operator.

Registrants of Soil Measurement Models (Agriculture Laboratories, University Agriculture Departments, and the like):

The registrants of soil measurement models are the parties that use experiments to calculate the control data C and the soil measurement model m required for accurately measuring soil properties in accordance with the type of soil and water content, and register such information in the soil model data base. These parties receive data use payments in accordance with the number of times the soil measurement model is utilized.

Application System Makers

The application system makers are the parties that receive the disclosure of the communication protocol with the soil model data base control system, information on the format of the data base and the like, acquire access approval to special data, pay use fees as the price thereof, and construct various application systems.

Users (General Farmers, Innovative Farmers, Agricultural Product Corporations, Leisure Farming Administration Groups)

The users are the parties that access the soil model data base, receive appropriate information and services related to their own fields, and pay use fees as the price thereof.

Environment-Oriented Consumers and Consumer Groups

The environment-oriented consumers and consumer groups input information on production sites and producers of agricultural products, and access the soil model data base. Then, the cleanness level or pollution level of the soil environment utilized in growing such products is read out. Further, the soil judgment results are read out. Then, these items are used to judge whether or not the products should be purchased.

Next, a description will be given for the function and use of the network system formed by each of the users described above. First, in accordance with a request submitted by the user to the soil model data base control system 95 for controlling the soil model data base, the soil model data base control system 95 carries out a prescribed process.

Namely, in the case where the user is a party that wants to use information stored in the soil model data base, because the user submits an information acquisition request, information matching the conditions of this information acquisition request is acquired from the soil model data base and supplied to the user. Further, in the case where the user is a party that wants to register information in the soil model data base, because the user submits an information registration request, the information contained in the registration request is registered in a related storage area, whereafter it becomes possible to utilize (supply) such registered information.

Further, in any of the utilization situations (information acquisition/registration) described above, history information (time of process execution, executor ID, process contents, type and quantity of acquired/registered information) of the processes carried out therefor is created and recorded. Namely, the soil model data base control system 95 includes a soil model data base and a history information storage portion for storing the history information described above.

Then, at a prescribed timing (e.g., monthly or the like), a process for settling utilization fees such as use fees, data use fees, registration fees, advertisement fees and the like is carried out for each user who utilizes the soil model data base based on the history information recorded in the history information storage portion. Namely, the amount of money that should be paid and the amount of money that should be collected are calculated, and then a payment process is carried out based on the amount of money that should be paid, and a billing process and a collection process are executed based on the amount of money that should be collected.

Further, the collection and payment of fees can be carried out by cash such as by depositing or withdrawing money from a known bank account or the like, or by electronic transfer. Furthermore, an arrangement of electronic money and utilization points that can be used on the network may be created, and then the fees can be settled by such utilization points and the like. When this is carried out, in particular, in the case where the user carries out both collection and payment of utilization fees, the settlement process becomes easy, and by registering important information without carrying out an actual cash settlement, it is possible to acquire other information that is required.

Figure 29:
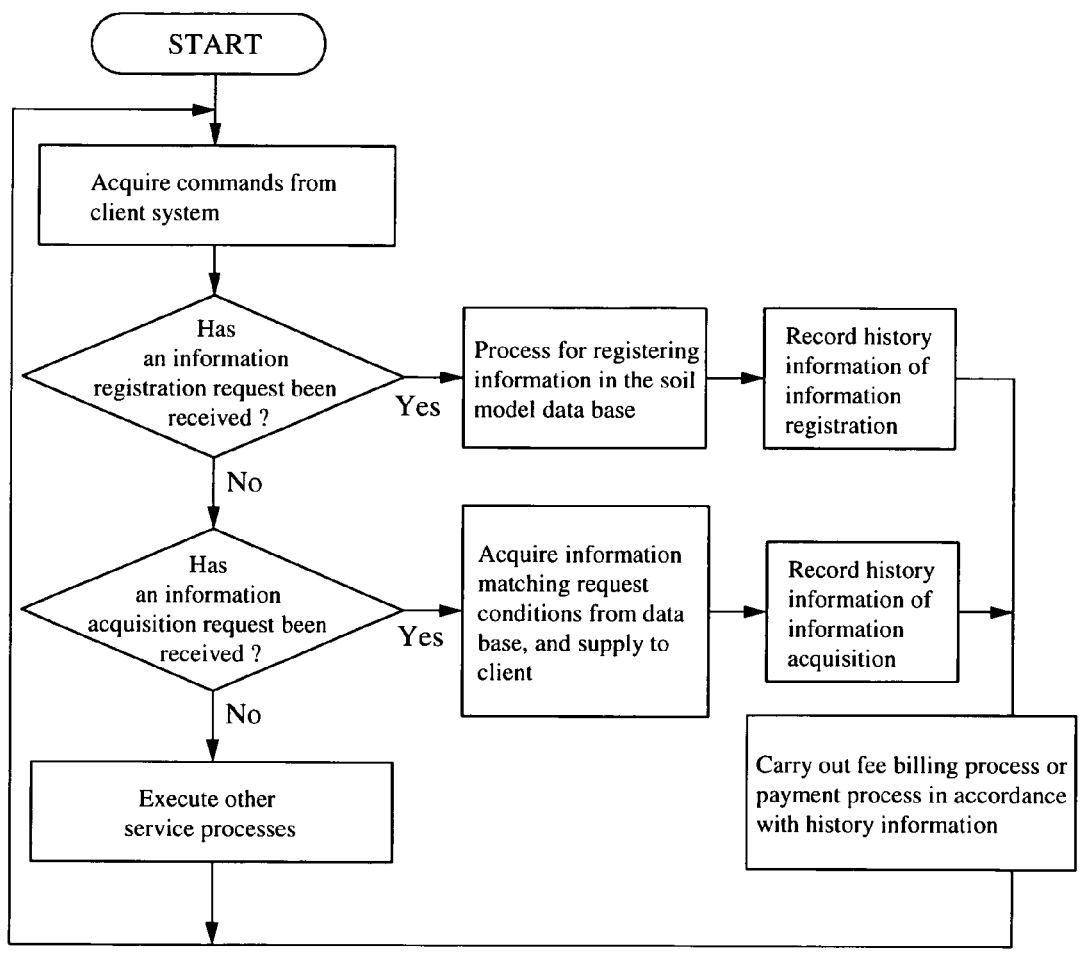
FIG. 29 is a flow chart for describing the function of the soil model data base management system.

Further, the function of the computer system for executing each of the processes described above, and more specifically the function of the soil model data base control system 95 can be carried out by the flow chart shown in FIG. 29.

Further, in order to effectively implement the system (business model) described above, the following conditions are preferably satisfied.

Accurate data should be recorded in the soil model data base.

An abundant amount of data should be recorded in the soil model data base, and this data should be updated frequently.

The format of the control data and the soil measurement model should be standardized and suited to many soil measuring apparatuses.

It should be easy to access the soil model data base, and the fee should be a low price.

Information on the actual results of using registered data should be accurate, and the data use fee should be properly paid.

Figure 30:
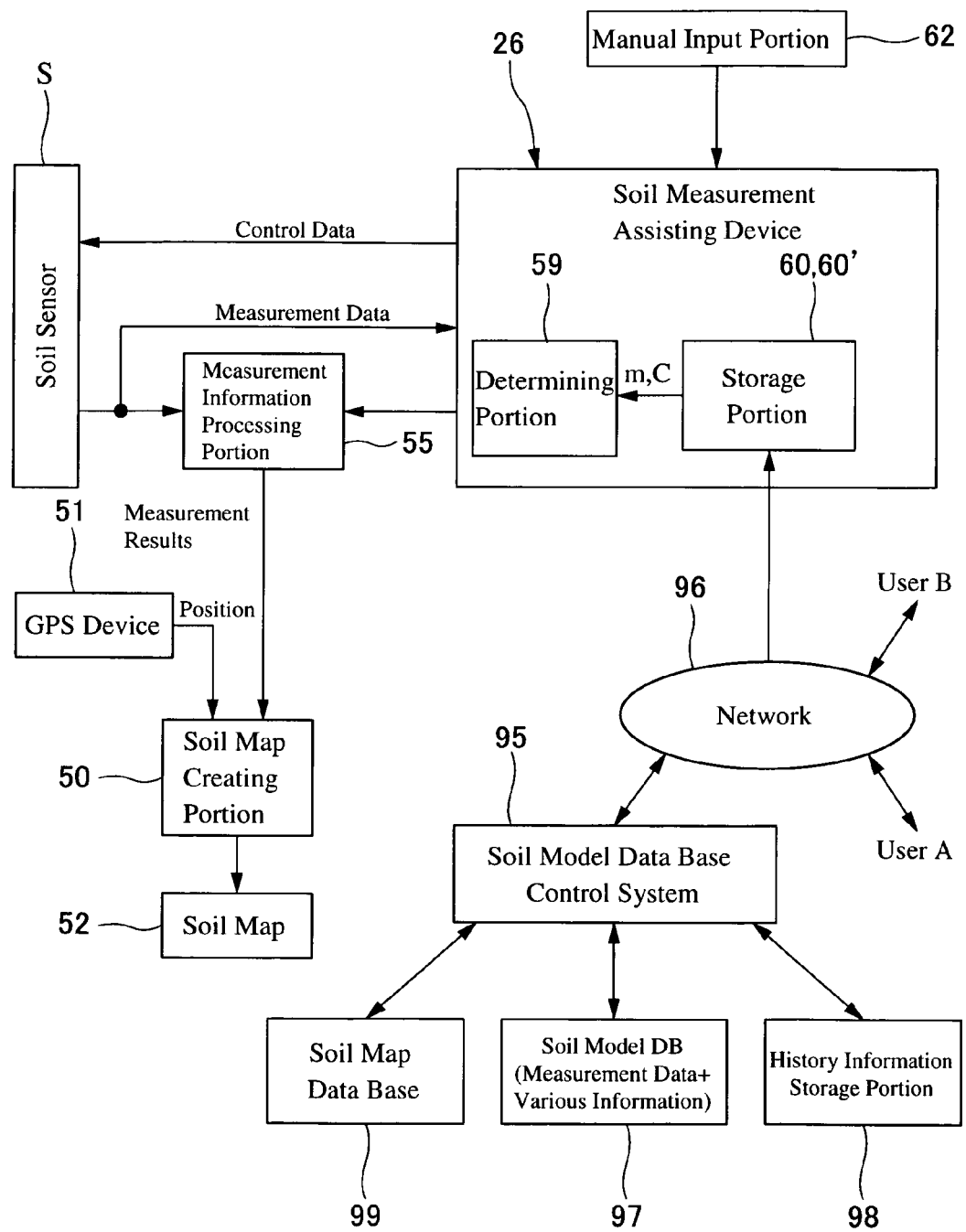
FIG. 30 is a drawing showing a specific application example of a network system which includes a soil model data base management system.

FIG. 30 shows a network structure from the viewpoint of a general farmer or the like who uses the soil measurement assisting device 26 as a user who uses the soil model data base by being connected to the network system described above.

As shown in the drawing, because the soil model data base control system 95 is connected to a network 96, by connecting the soil assisting device 26 to the network 96, the soil model data base control system 95 and the soil assisting device 26 will be connected via the network 96, and this makes it possible to transmit and receive data.

Further, the soil model data base control system 95 is equipped with a soil model data base 97 (which is the data base shown in FIG. 27) which stores information supplied from various users, and a history information storage portion 98.

Then, in the case of required information, namely, in the case where only the soil model m and the measurement conditions (control data) C are required, the soil assisting device 26 issues an acquisition request for the latest edition of such information to the soil model data base control system 95, and after this is received, the supplied information is stored in the soil measurement data storage portion 60. Thereafter, measurements of the soil components and the like are carried out based on the acquired information.

Further, in the case where the required information includes other information in addition to the soil model m and the measurement conditions (control data) C, an acquisition request for corresponding data registered in the soil model data base 97 is carried out, and after this is received, the supplied information is stored in its own soil model data base 60'. Thereafter, based on this acquired information, measurements of the soil components and the like are carried out, and the provision of required information is received.

On the other hand, the calculated soil map measured by the soil measurement assisting device 26 based on the soil model data acquired as described above is normally used for one's own farm working, and it becomes possible to simultaneously pursue both "environmental pollution countermeasures" and "soil preparation agriculture." Further, this calculated soil map is sent to the soil model data base control system 95, and it is also possible to register the soil map in a soil map data base 99 controlled by the soil model data base control system 95.

When this is done, because it is possible to easily obtain the distribution state of types of soil nationwide, such arrangement is preferred. As for information registered at this time, only the types of soil may be registered, or the types of soil and soil components information may be correlated and registered. Further, because the types of soil and the like can be used later as useful information, the fee for the information supplied can be paid for in accordance with registration, and it is possible to collect the fee for the used data from the user who uses the soil map.

Further, although the soil map data base 99 was described as being separate from the soil model data base 95 for convenience sake, these can be treated as one element, namely, the soil map data base can be included in the soil model data base.

Each of the embodiments described above were described with the assumption that they are included in devices, but it is also possible to provide a program for executing each of the processes described above (e.g., processes for executing the flow charts shown in each drawing) by a computer, wherein such program is supplied by being recorded on a prescribed recording medium.

Figure 31:
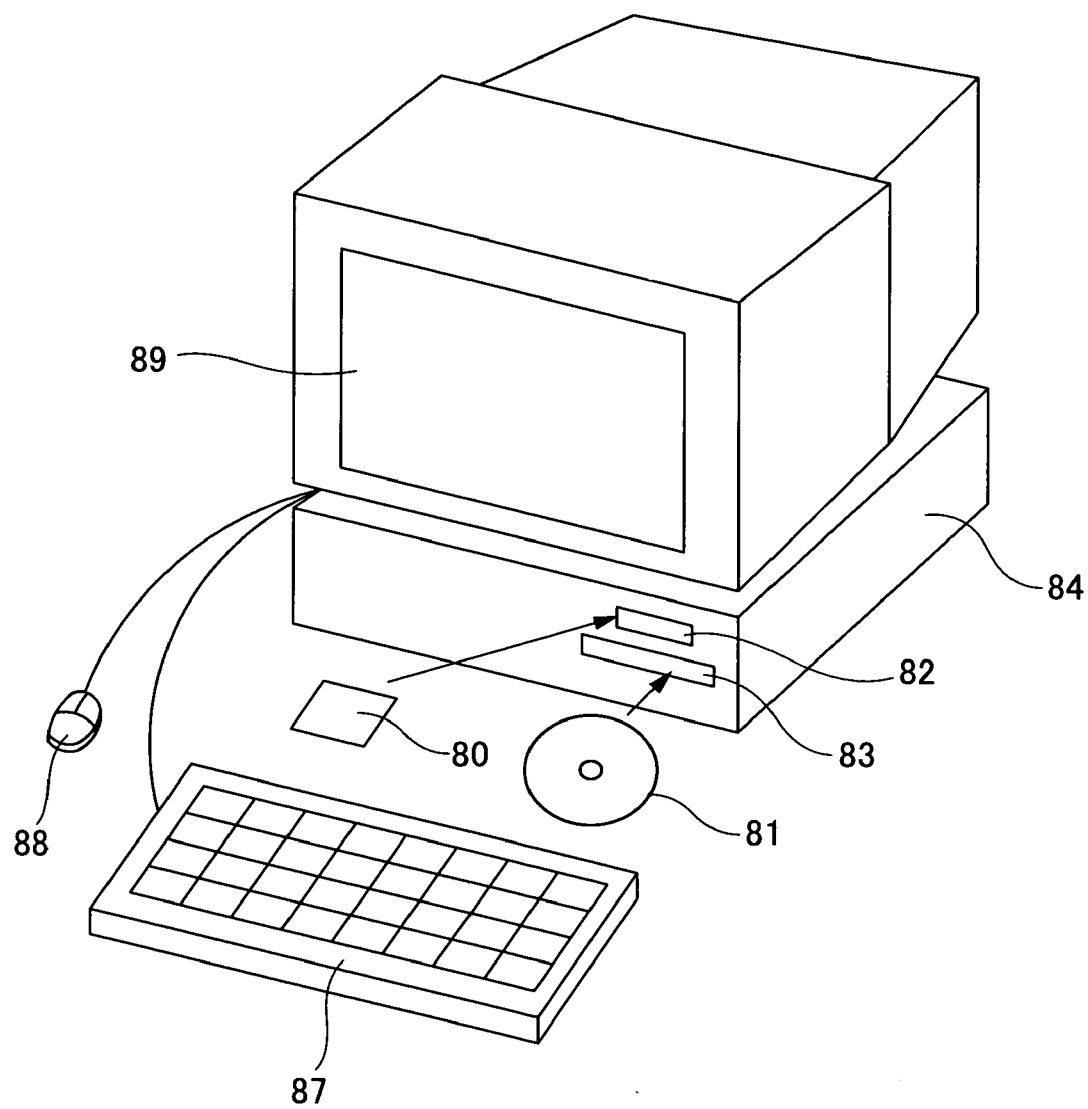
FIG. 31 is a drawing showing a system structure for =implementing a recording medium according to the present invention.
Figure 32:
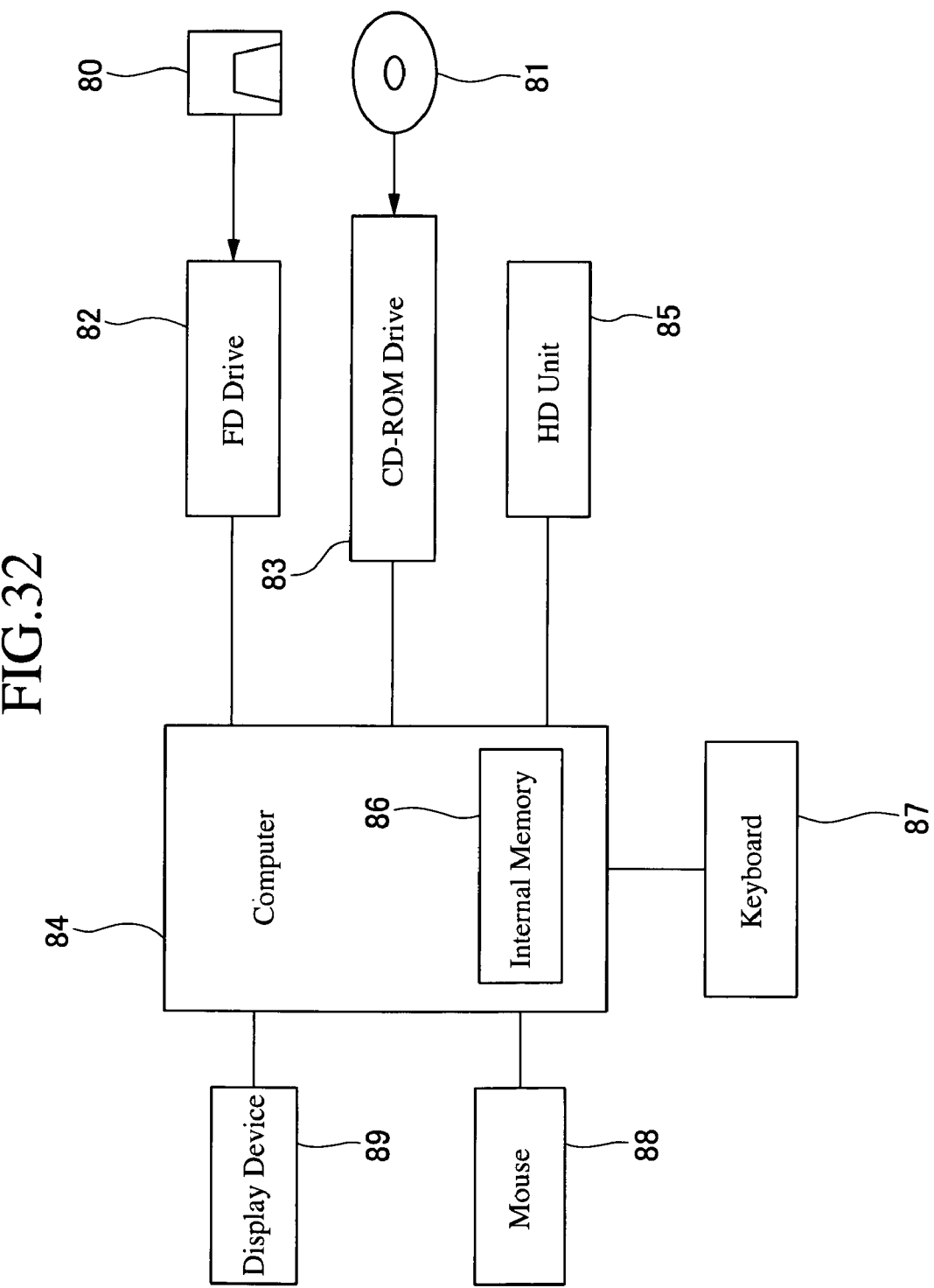
FIG. 32 is a drawing showing a system structure for implementing a recording medium according to the present invention.

Namely, as shown in FIG. 31 and FIG. 32, a floppy disk (FD) 80 and a CD-ROM 81 or the like serve as recording mediums, and the programs stored on such recording mediums 80, 81 are installed in a HD unit 85 connected (internally) to a computer 84 via a FD drive 82 and a CD-ROM drive 83, and in this way, the computer 84 forms the apparatus described in the embodiments described above.

Specifically, the measurement information processing portion 55, the feature extracting portion 56, the water content ratio detecting portion 57 (water content detecting portion 57'), the type-of-soil discriminating portion 58, the determining portion 59 and the like in the embodiments are installed in the HD unit 85, and transferred from the HD unit 85 to an internal memory 86 at each time of use for example, whereby it is possible to carry out various processes therein at high speed. Further, the soil measurement data storage portion 60 and the GIS data storage portion 63 are formed by the recording devices and recording mediums of the HD unit 85, the CD-ROM 83 and the like.

Further, a keyboard 87 and a mouse 88 function as input devices, and data which is manually inputted is supplied via these input devices. Further, the numeral 89 in the drawings denotes a display device which displays analysis results and the like, and which displays position information and the like for reading out manually inputted data and GIS data, and the contents at the time various control commands are inputted, whereby it is possible to carry out confirmation.

INDUSTRIAL APPLICATION

As described above, in the soil measuring apparatus, the measuring method and the recording medium on which programs are recorded according to the present invention, it is possible to accurately calculate soil properties for soils having different water contents and types of soil. Further, in the case where a soil measurement assisting function is provided, because it is possible to automatically establish measurement data and a model suited to the measurement site, it is possible to carry out measurements efficiently. Further, when a map correlated with the position information and the soil properties is created, because it is possible to thereafter use this map to create various plans, such arrangement is preferred.

Further, the apparatus main body portion for measuring and analyzing soil properties and the assisting device which establishes models and the like at the time of measurements may be integrated together or arranged separately. Further, in the case where a separation arrangement is possible, the utilization situations are diversified, and a higher convenience is achieved.

Further, in the soil measurement assisting apparatus, the assisting method and the recording medium on which programs are recorded according to the present invention, it is possible to automatically establish the model and measurement conditions of the measurement site required at the time soil properties are measured. Consequently, it is possible to carry out highly accurate analysis of soil properties efficiently.

Furthermore, in the case where a function for automatically establishing information related to the type of soil and the water content is provided, it is possible to calculate soil properties at a high efficiency with no mistakes. Of course, in the present invention, even without the function for automatic establishment, by using data of a previous type of soil in such case, the process for detecting the type of soil at the time of measurements becomes unnecessary, and this makes it possible to shorten the process time.

Moreover, as for the recording medium which records prescribed data, by using this recording medium for reading out data by a computer, the measurement conditions and the model suited to the condition of the site where the soil is measured can be easily read out and used for soil measurements, and this makes it possible to carry out highly accurate soil analysis. Furthermore, when soil correlated information is included in the recorded data, information required for the person related to the soil can be efficiently supplied or inputted/outputted.

Further, in the present invention, because soil properties can be measured in real time, and because it is possible to calculate the currently required insufficient substances and quantities thereof for such measured soil, it is possible to carry out efficient soil preparation, and the application of agricultural chemicals and other soil improvements and the like can be carried out.

Further, as for the application amount control device, the application amount determining device and the methods thereof according to the present invention, when determining the application amount of the above-described substances, because such determination can be carried out by considering environmental standards, it is possible to carry out environmental preservation. Namely, it is possible to simultaneously pursue both "environmental pollution countermeasures" and "soil preparation agriculture."

What is claimed is:

1. A soil measuring method that uses a soil measuring apparatus to measure properties of a soil, including the steps of:
   obtaining information related to a soil type and a water content of a measurement site;
   determining a model based on the soil type and the water content;
   acquiring measurement data using a soil sensor based on information related to at least one parameter selected from the soil type and the water content; and
   calculating the properties of the soil using said acquired measurement data in the model.

2. A soil measuring apparatus, comprising:
   detecting means for acquiring measurement data from a soil of a measurement site; and
   processing means for calculating soil properties based on said measurement data acquired by said detecting means,
   wherein the processing means comprises a model for processing said measurement data, and wherein the model is determined based on information related to a soil type and a water content of a soil of the measurement site.

3. The soil measuring apparatus of claim 2, wherein the processing means further comprises a soil measurement assisting program for determining said model and measurement conditions based on the at least one parameter selected from the soil type and the water content.

4. The soil measuring apparatus of claim 2 or claim 3, further comprising map creating means for creating a soil map based on soil properties calculated by the processing means and position information of the measurement site.

5. A computer readable recording medium comprising a soil measurement assisting program that includes commands for a computer to execute:
   a process for establishing a model based on a soil type and a water content of a soil of a measurement site; and
   a process for receiving measurement data from a soil sensor, and for calculating soil properties from the received measurement data based on said model.

6. A soil measurement assisting method for a soil measuring apparatus that measures properties of a soil, including the steps of:
   acquiring initial measurement data related to a soil type and a water content of a soil of a measurement site; and
   determining measurement conditions for further measurements and a model for calculating the properties of the soil, wherein the determining is based on the acquired initial measurement data related to the soil type and the water content and information stored on a storage means on the soil measuring apparatus.

7. A soil measurement assisting method for a soil measuring apparatus that measures properties of a soil, including the steps of:
   acquiring initial measurement data related a soil type and a water content of a soil of a measurement site; and
   determining measurement conditions for further measurements based on the acquired initial measurement data related to the soil type and the water content and information stored on a storage means on the soil measuring apparatus.

8. A soil measurement assisting method for a soil measuring apparatus that measures properties of a soil, including the steps of:
   acquiring initial measurement data related to a soil type and a water content of a soil of a measurement site; and
   determining a model for calculating the properties of the soil based on the acquired initial measurement data related to the soil type and the water content and information stored on a storage means on the soil measuring apparatus.

9. A soil measurement assisting device for a soil measuring apparatus that measures properties of a soil, comprising:
   storage means for storing soil measurement data correlated with at least one selected from a soil type, information related to a water content of the soil, a model for calculating soil properties, and measurement conditions for obtaining measurement data that will be inputted into the model;
   determining means for acquiring initial measurement data related to the soil type and the water content of a measurement site, and for accessing said storage means to determine measurement conditions and the model for calculating the properties of the soil based on the acquired initial measurement data related to the soil type and the water content; and
   means for outputting said measurement conditions and the model determined by the determining means.

10. A soil measurement assisting device for a soil measuring apparatus that measures properties of a soil, comprising:
    storage means for storing soil measurement data correlated with at least one selected from a soil type, information related to a water content of the soil, and measurement conditions for obtaining measurement data that will be inputted into a model for calculating soil properties;
    determining means for acquiring initial measurement data related to the soil type and the water content of a measurement site, and for accessing said storage means to determine measurement conditions based on the acquired initial measurement data related to the said soil type and said water content; and
    means for outputting said measurement conditions determined by the determining means.

11. A soil measurement assisting device for a soil measuring apparatus that measures properties of a soil, comprising:
    storage means for storing soil measurement data correlated with at least one selected from a soil type, information related to a water content of the soil, and a model for calculating soil properties;
    determining means for acquiring initial measurement data related to the soil type and the water content of a measurement site, and for accessing said storage means to determine the model for calculating the soil properties based on the acquired initial measurement data related to the soil type and the water content; and
    means for outputting said model determined by the determining means.

12. The soil measurement assisting device of any one of claim 9 through claim 11, further comprising a type-of-soil detecting means for calculating said soil type based on the initial measurement data, and for supplying the calculated soil type to the determining means.

13. The soil measurement assisting device of any one of claim 9 through claim 11, further comprising a water content detecting means for calculating said water content based on the initial measurement data, and for supplying the calculated water content to said determining means.

14. The soil measurement assisting device of any one of claim 9 through claim 11, further comprising a water content detecting means for calculating said water content based on the initial measurement data and a preliminary soil type estimated from a clay content of the soil of the measurement site, and for supplying the calculated water content to said determining means.

15. The soil measurement assisting device of any one of claim 9 through claim 11, wherein said soil type is determined from a database that stores previous measurements.

16. A soil measurement assisting method for a soil measuring apparatus that measures properties of a soil, comprising the steps of:
    acquiring a first set of measurement data related to optical properties of a measurement site;
    determining a preliminary soil model based on the acquired first set of measurement data and information stored in a storage means on the soil measuring apparatus;
    reading out the preliminary soil model;
    acquiring a second set of measurement data related to chemical components of the soil; and
    modifying the preliminary model based on the second set of measurement data.

17. A recording medium that can be read by a computer and that stores a soil measurement assisting program that includes commands for the computer to execute:
  a process that acquires initial measurement data related to a soil type and a water content of a soil of a measurement site;
  a process that, based on the acquired initial measurement data, accesses a storage region that stores information related to the soil type, the information related to the water content of the soil, a model for calculating soil properties, and measurement conditions for acquiring further measurement data to be inputted into the model; and
  a process that outputs a set of suitable measurement conditions and the model determined based on the initial measurement data related to the soil type and the water content.

18. A recording medium that can be read by a computer and that stores a soil measurement assisting program that includes commands for the computer to execute:
  a process that acquires initial measurement data related to a soil type and a water content of a measurement site;
  a process that, based on the acquired initial measurement data, accesses a storage region that stores information related to the soil type, the information related to the water content, and measurement conditions for acquiring further measurement data to be inputted into a model for calculating soil properties; and
  a process that outputs a set of suitable measurement conditions determined based on the initial measurement data related to the soil type and the water content.

19. A recording medium that can be read by a computer and that stores a soil measurement assisting program that includes commands for the computer to execute:
  a process that acquires initial measurement data related to a soil type and a water content of a measurement site;
  a process that, based on the acquired initial measurement data, accesses a storage region that stores information related to soil types, water contents of soils, and models for calculating soil properties, and determines, based on the initial measurements data related to the soil type and the water content, a suitable model for calculating soil properties; and
  a process that outputs the suitable model.

20. The recording medium that can be read by a computer according to any one of claim 17~claim 19, further comprising a program that executes at least one process selected from a process that calculates said soil type based on the initial measurement data of a measurement site, and a process that calculates the water content based on the initial measurement data.

21. A soil measuring apparatus, comprising:
  a soil measuring apparatus main body equipped with detecting means that acquires measurement data from a soil of a measurement site, and processing means that calculates soil properties based on said measurement data; and
  a soil measurement assisting device that determines, and then outputs to said soil measuring apparatus main body, a soil type of the measurement site, a model for carrying out processing by said processing means based on information related to a water content of the soil, and measurement conditions for acquiring further measurement data that will be inputted into the model.

22. A recording medium that can be read by a computer and that stores at least one selected from a soil type, information related to a water content of a soil, a model for calculating soil properties, and soil measurement data correlated with measurement conditions to be inputted into the model.

23. The recording medium of claim 22, wherein said soil measurement data is further correlated with a name of a measurement object property.

24. The recording medium of claim 22, wherein said soil measurement data is further correlated with a measurement method.

25. The recording medium of claim 22, wherein said soil measurement data is further correlated with a name of a measurement object property and a measurement method.

26. A recording medium that can be read by a computer and that stores at least one selected from a soil type, information related to a water content of a soil, soil measurement data for calculating soil properties, and soil correlation information in a constructed state that enables output.

27. A soil model database control system that accesses, updates and reads out stored contents of a soil model database, wherein:
  the soil model database stores one parameter selected from a soil type, information related to a water content of a soil, soil measurement data for calculating soil properties, and soil correlation information, the soil model database control system comprising:
  a function for supplying recorded information in response to a request received from a user, and for updating contents of the soil model database.

28. The soil measurement assisting device of claim 12, further comprising a water content detecting means for calculating the water content based on the initial measurement data and for supplying the calculated water content to said determining means.

29. The soil measurement assisting device of claim 12, further comprising a water content detecting means for calculating the water content based on the initial measurement data and a preliminary soil type estimated from a clay content of the soil of the measurement site, and for supplying the calculated water content to the determining means.

30. The soil measurement assisting device of claim 13, further comprising a water content detecting means for calculating the water content based on the initial measurement data and a preliminary soil type estimated from a clay content of the soil of the measurement site, and for supplying the calculated water content to the determining means.

31. The soil measurement assisting device of claim 12, wherein said soil type is determined from a database that stores previous measurements.

32. The soil measurement assisting device of claim 13, wherein said soil type is determined from a database that stores previous measurements.

33. The soil measurement assisting device of claim 14, wherein said soil type is determined from a database that stores previous measurements.

* * * * *